(12) United States Patent
Blasco-Baque et al.

(10) Patent No.: US 10,925,951 B2
(45) Date of Patent: Feb. 23, 2021

(54) VACCINATION AGAINST DIABETES, OBESITY AND COMPLICATIONS THEREOF

(71) Applicants: INSTITUT NATIONAL DE LA SANTE ET DE LA RECHERCHE MEDICALE (INSERM), Paris (FR); UNIVERSITE PAUL SABATIER TOULOUSE III, Toulouse (FR); CENTRE HOSPITALIER UNIVERSITAIRE DE TOULOUSE, Toulouse (FR)

(72) Inventors: Vincent Blasco-Baque, Toulouse (FR); Lucile Garidou, Toulouse (FR); Rémy Burcelin, Toulouse (FR)

(73) Assignees: INSTITUT NATIONAL DE LA SANTE ET DE LA RECHERCHE MEDICALE (INSERM), Paris (FR); UNIVERSITE PAUL SABATIER TOULOUSE III, Toulouse (FR); CENTRE HOSPITALIER UNIVERSITAIRE DE MONTPELLIER, Toulouse (FR)

( * ) Notice: Subject to any disclaimer, the term of this patent is extended or adjusted under 35 U.S.C. 154(b) by 0 days.

(21) Appl. No.: 16/061,830

(22) PCT Filed: Dec. 15, 2016

(86) PCT No.: PCT/EP2016/081157
§ 371 (c)(1),
(2) Date: Jun. 13, 2018

(87) PCT Pub. No.: WO2017/102927
PCT Pub. Date: Jun. 22, 2017

(65) Prior Publication Data
US 2018/0369353 A1 Dec. 27, 2018

(30) Foreign Application Priority Data

Dec. 15, 2015 (EP) .................................. 15307004

(51) Int. Cl.
| | | |
|---|---|---|
| A61K 39/02 | (2006.01) | |
| A61P 3/04 | (2006.01) | |
| A61P 3/10 | (2006.01) | |
| A61P 9/12 | (2006.01) | |
| A61K 39/114 | (2006.01) | |
| A61K 39/00 | (2006.01) | |
| A61P 31/00 | (2006.01) | |

(52) U.S. Cl.
CPC ........ A61K 39/0216 (2013.01); A61K 39/114 (2013.01); A61P 3/04 (2018.01); A61P 3/10 (2018.01); A61P 9/12 (2018.01); *A61K 2039/51* (2013.01); *A61K 2039/521* (2013.01); *A61K 2039/522* (2013.01); *A61P 31/00* (2018.01)

(58) Field of Classification Search
None
See application file for complete search history.

(56) References Cited

U.S. PATENT DOCUMENTS

| | | | |
|---|---|---|---|
| 6,254,863 B1* | 7/2001 | Fletcher ............. | A61K 39/0216 424/200.1 |
| 2017/0014468 A1* | 1/2017 | Dominy ................. | A61K 38/05 |

FOREIGN PATENT DOCUMENTS

| | | |
|---|---|---|
| CN | 101 791 405 B | 1/2012 |
| WO | 2004/045550 A2 | 6/2004 |
| WO | 2011/103633 A1 | 9/2011 |

OTHER PUBLICATIONS

Bowie et al. (Science, 1990, 247:1306-1310.*
Burgess et al. (J. Cell Biol. 111:2129-2138, 1990).*
Lazar et al. (Mol. Cell. Biol., 8:1247-1252, 1988).*
Liu et al (Vaccine, 27:1589-1595, 2009).*
Salomon et al., "Diet-induced obesity in mice causes changes in immune responses and bone loss manifested by bacterial challenge", Proceedings of the National Academy of Sciences of the United States of America, Dec. 18, 2007, pp. 20466-20471, vol. 104, No. 51.
Santos Tunes et al., "Impact of periodontitis on the diabetes-related inflammatory status", Journal (Canadian Dental Association), 2010, p. a35, vol. 76.
Persson et al., "Immunization against Porphyromonas gingivalis inhibits progression of experimental periodontitis in nonhuman primates", Infection and Immunity, Mar. 1, 1994, pp. 1026-1031, vol. 62, No. 3, American Society for Microbiology, US.
Han et al., "DNA-based adaptive immunity protect host from infection-associated periodontal bone resorption via recognition of Porphyromonas gingivalisvirulence component", Vaccine, Sep. 16, 2013, pp. 297-303, vol. 32, No. 2.

(Continued)

*Primary Examiner* — Brian Gangle
(74) *Attorney, Agent, or Firm* — W&C IP

(57) ABSTRACT

The present invention concerns a composition comprising at least one prophylactically or therapeutically active agent selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a c DNA from *Porphyromonas gingivalis*, for use as a vaccine for preventing or treating periodontitis, diabetes, obesity and/or complications thereof in a subject. The present invention also concerns an isolated antibody having specificity for *Porphyromonas gingivalis* for use for preventing or treating periodontitis, diabetes, obesity and/or complications thereof in a subject.

1 Claim, 18 Drawing Sheets
Specification includes a Sequence Listing.

(56) References Cited

OTHER PUBLICATIONS

Parthasaradhi et al., "Periodontal Vaccines: A Sophisticated Treatment Design in the Future?", Biomed Pharmacol J, Oct. 2015, pp. 359-363, vol. 8.

Hayashi et al., "Porphyromonas gingivalis accelerates inflammatory atherosclerosis in the innominate artery of ApoE deficient mice", Atherosclerosis, Dec. 10, 2010, pp. 52-59, vol. 215, No. 1, Elsevier Ireland LTD, IE.

Hagiwara et al., "Sublingual Vaccine with GroEL Attenuates Atherosclerosis", Journal of Dental Research, Feb. 19, 2014, pp. 382-387, vol. 93, No. 4.

Koizumi et al., "Nasal gingivalis Outer Membrane Protein Decreases P. gingivalis-Induced Atherosclerosis and Inflammation in Spontaneously Hyperlipidemic Mice", Infection and Immunity, Apr. 21, 2008, pp. 2958-2965, vol. 76, No. 7.

Arora et al., "Periodontal infection, impaired fasting glucose and impaired glucose tolerance: results from the Continuous National Health and Nutrition Examination Survey 2009-2010", Journal of Clinical Periodontology, May 25, 2014, pp. 643-652, vol. 41, No. 7.

Choi et al., "Association Between Periodontitis and Impaired Fasting Glucose and Diabetes", Diabetes Care, Jan. 7, 2011, pp. 381-386, vol. 34, No. 2.

Krejci et al., "Obesity and periodontitis: a link", General Dentistry, Jan. 1, 2013, p. 60.

Pischon et al., "Obesity, Inflammation, and Periodontal disease", J Dent Res, May 1, 2007, pp. 400-409, vol. 86, No. 5.

Polak et al., "Vaccination of mice with Porphyromonas gingivalis or Fusobacterium nucleatum modulates the inflammatory response, but fails to prevent experimental periodontitis", Journal of Clinical Periodontology Jul. 29, 2010, pp. 812-817, vol. 37, No. 9.

Blasco-Baque et al., "Periodontitis induced by Porphyromonas gingivalis drives periodontal microbiota dysbiosis and insulin resistance via an impaired adaptive immune response", GUT, Feb. 2, 2016, UK.

\* cited by examiner

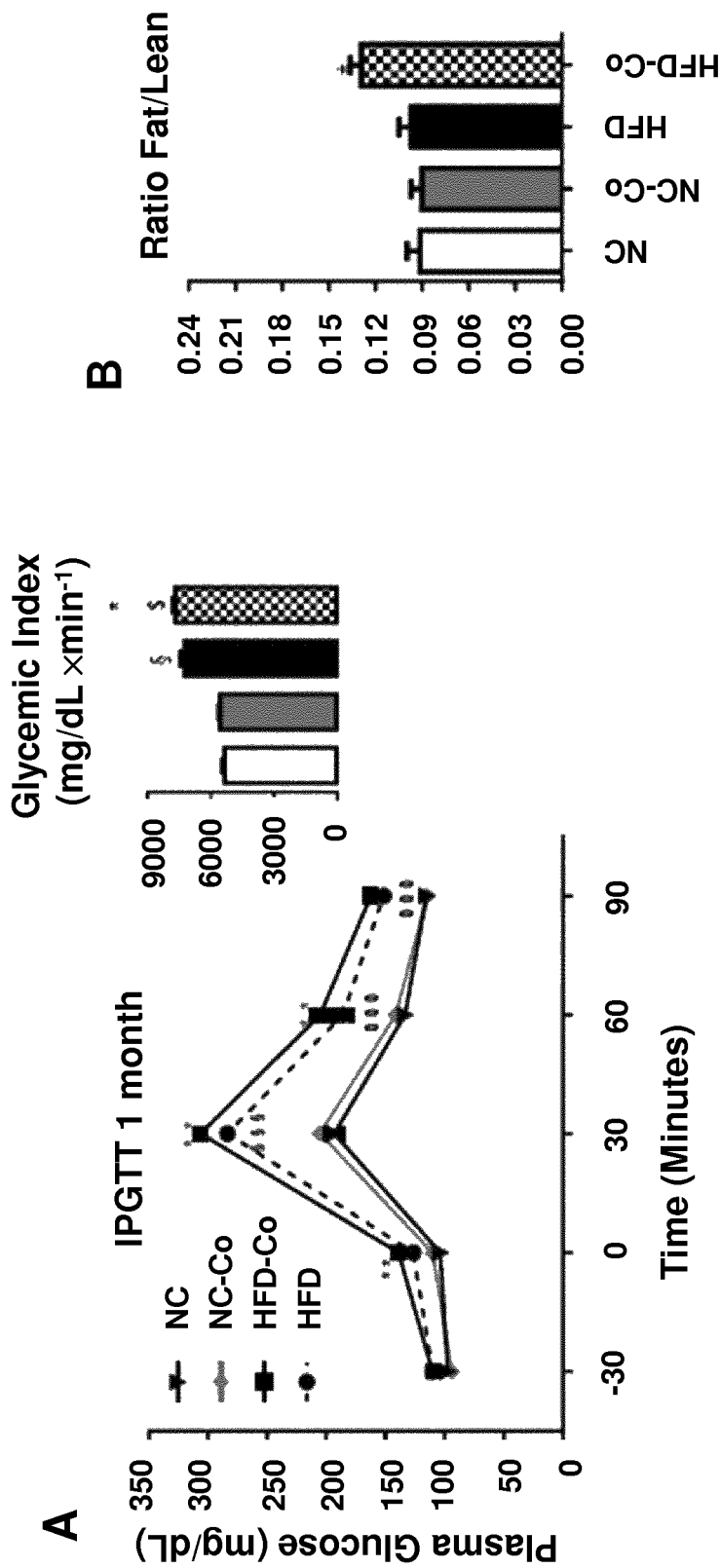
FIGURE 6 (beginning)

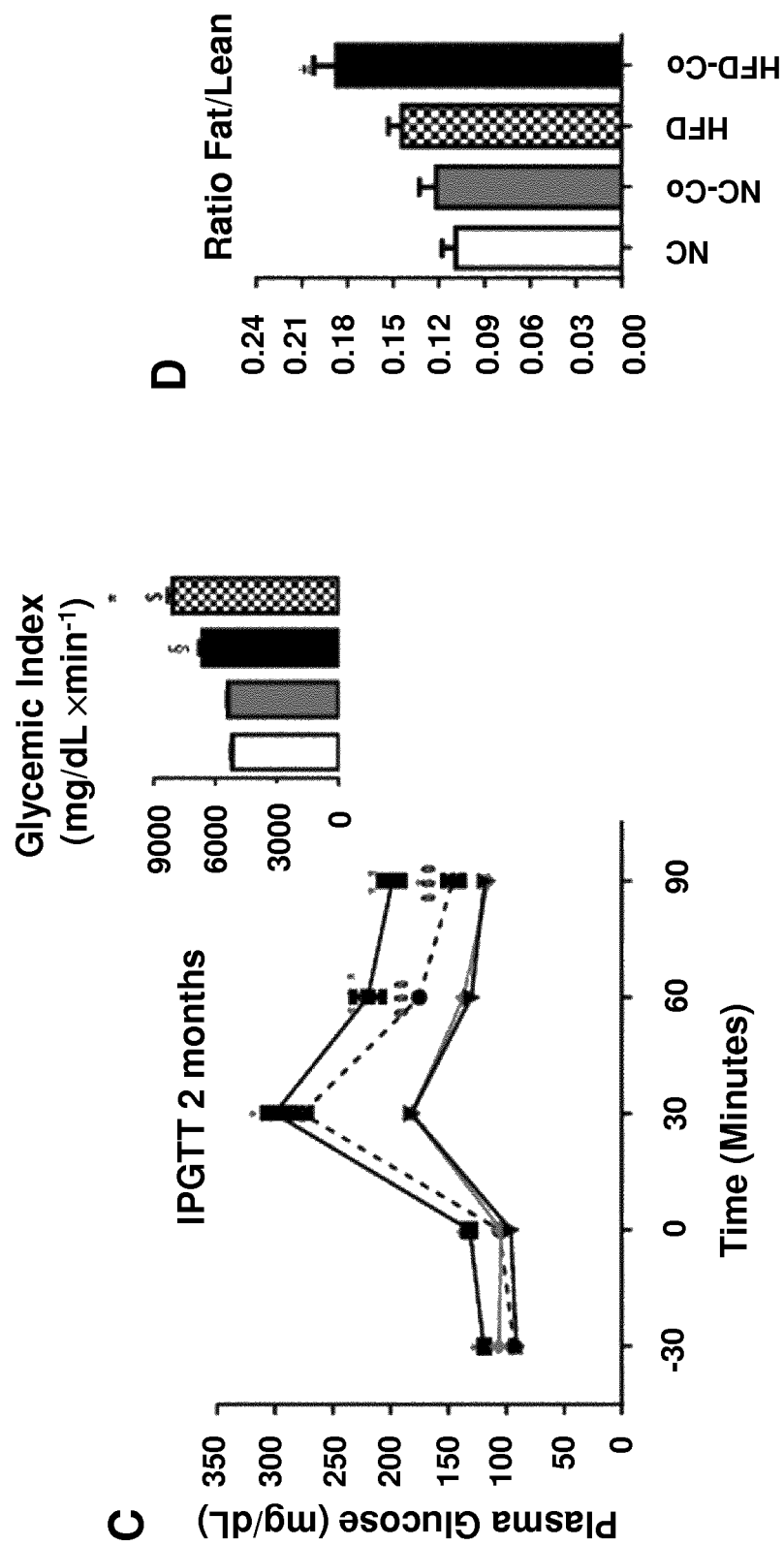
FIGURE 6 (continuing)

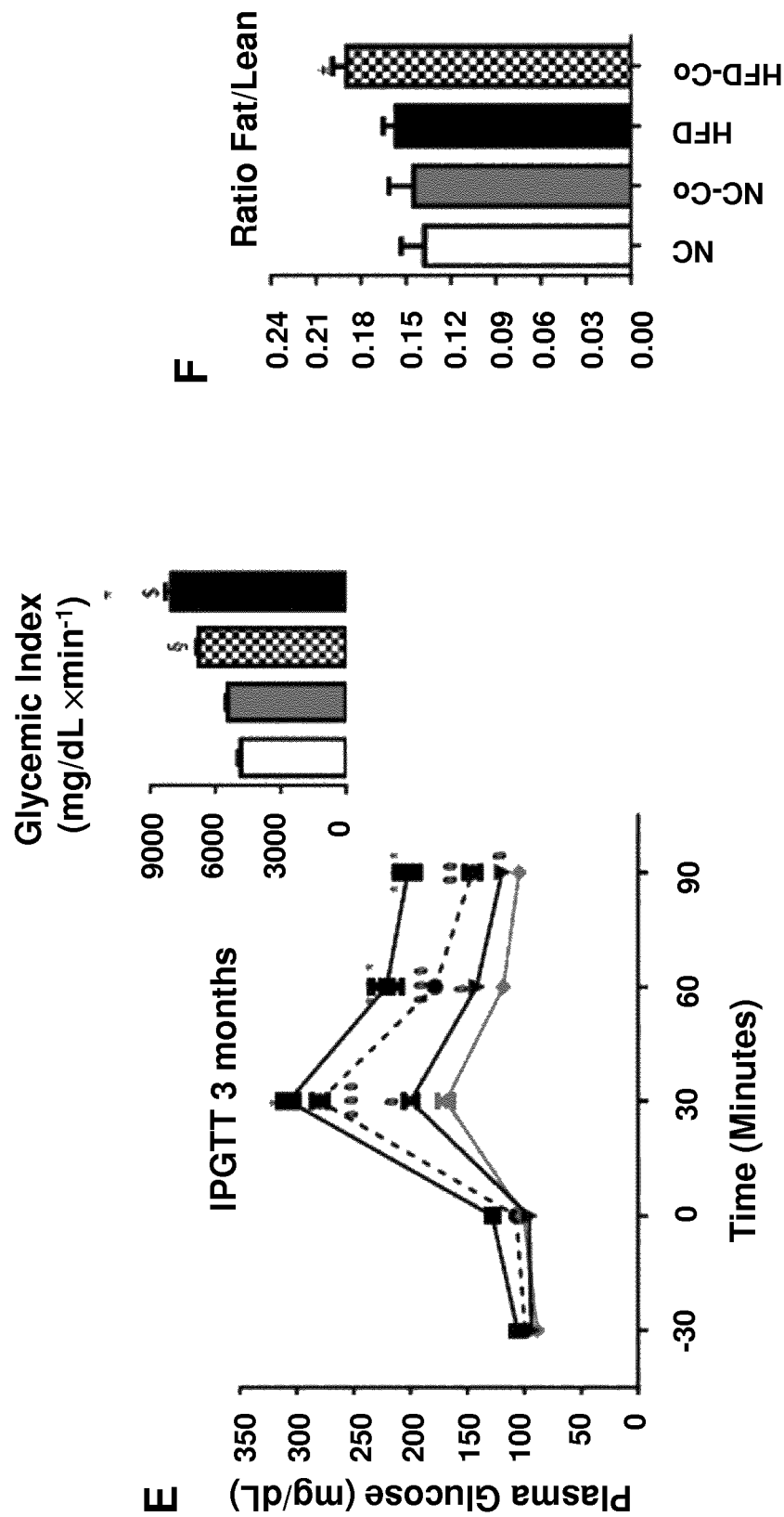
FIGURE 6 (end)

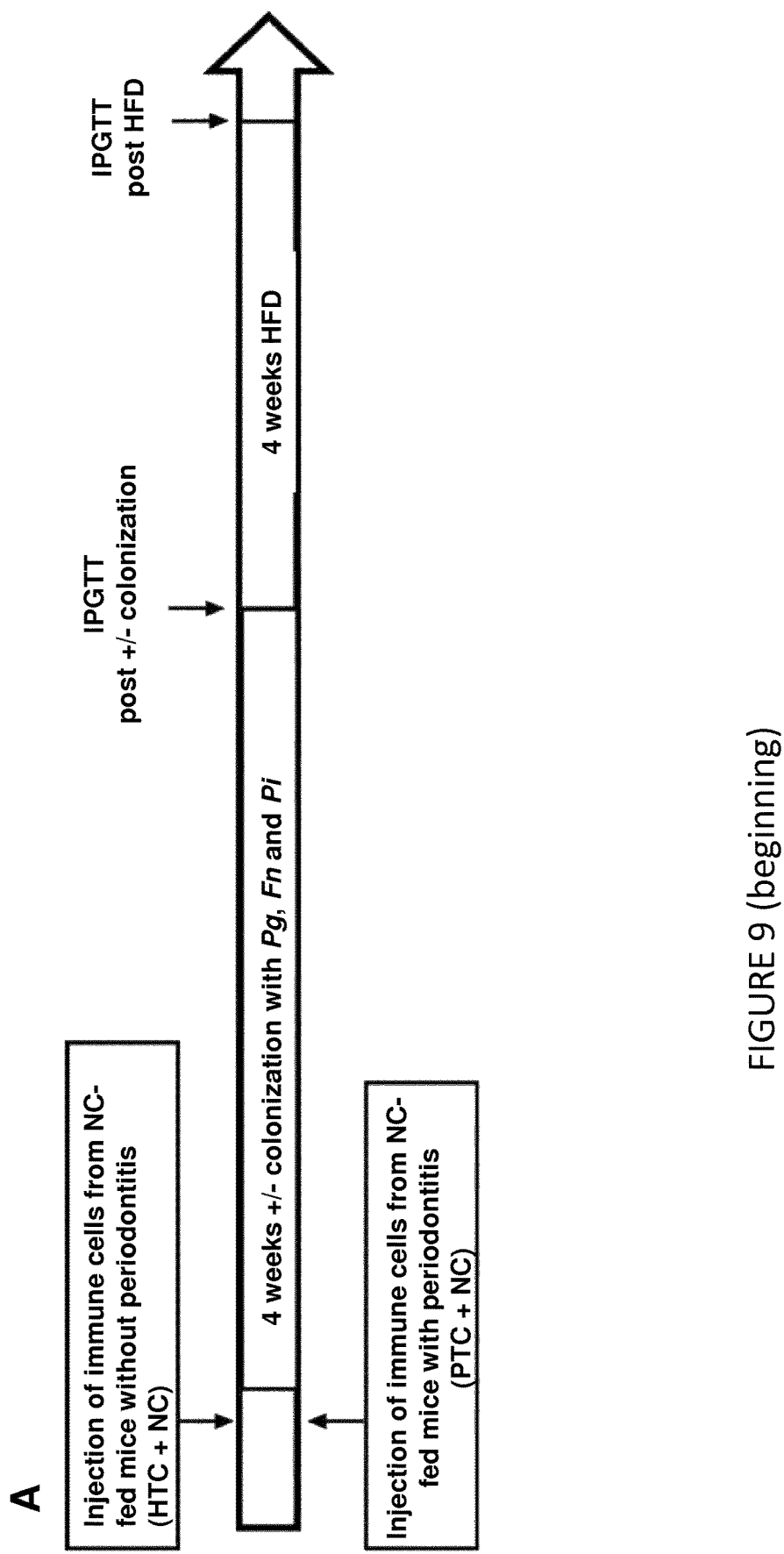
FIGURE 9 (beginning)

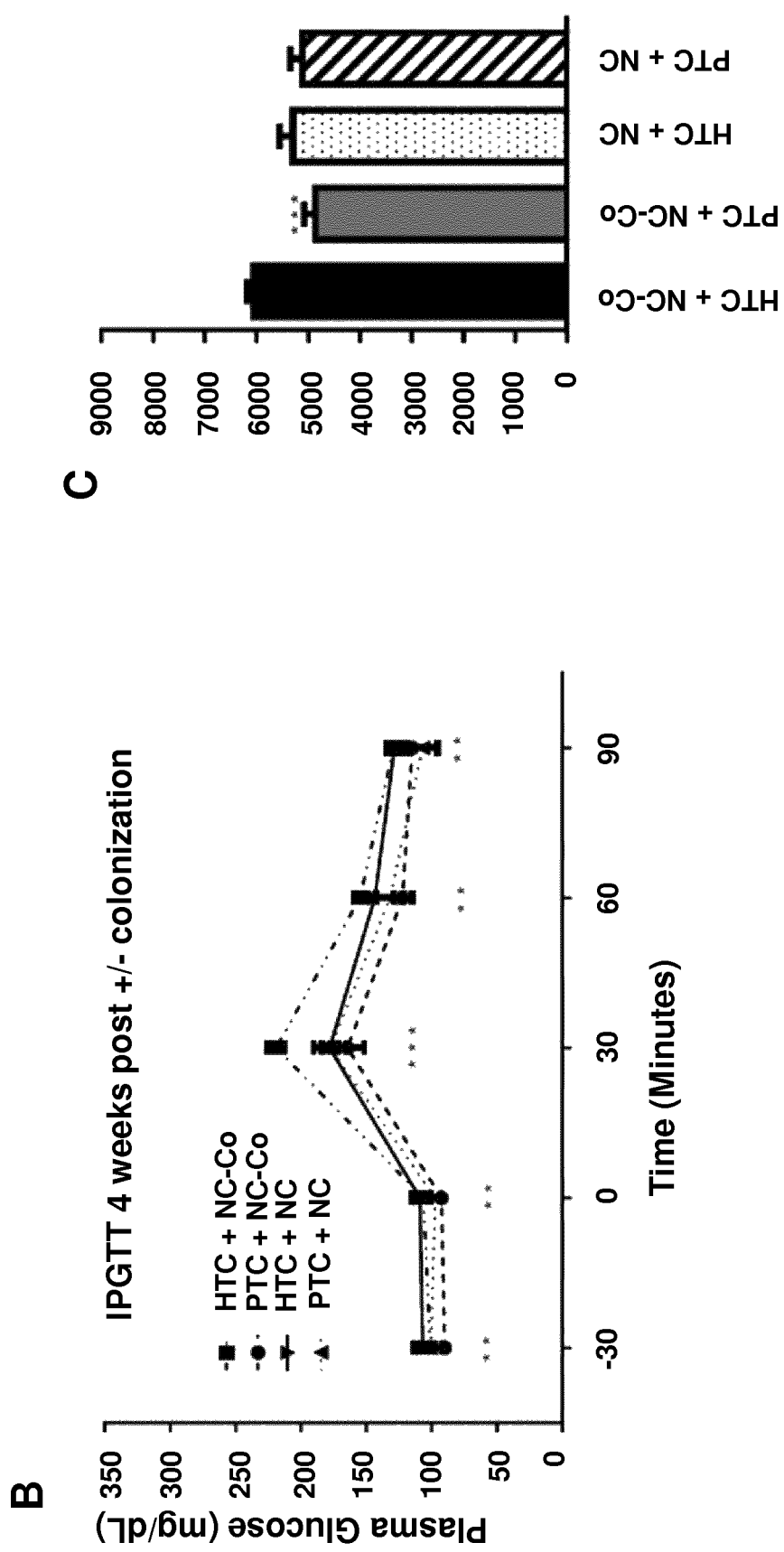
FIGURE 9 (end)

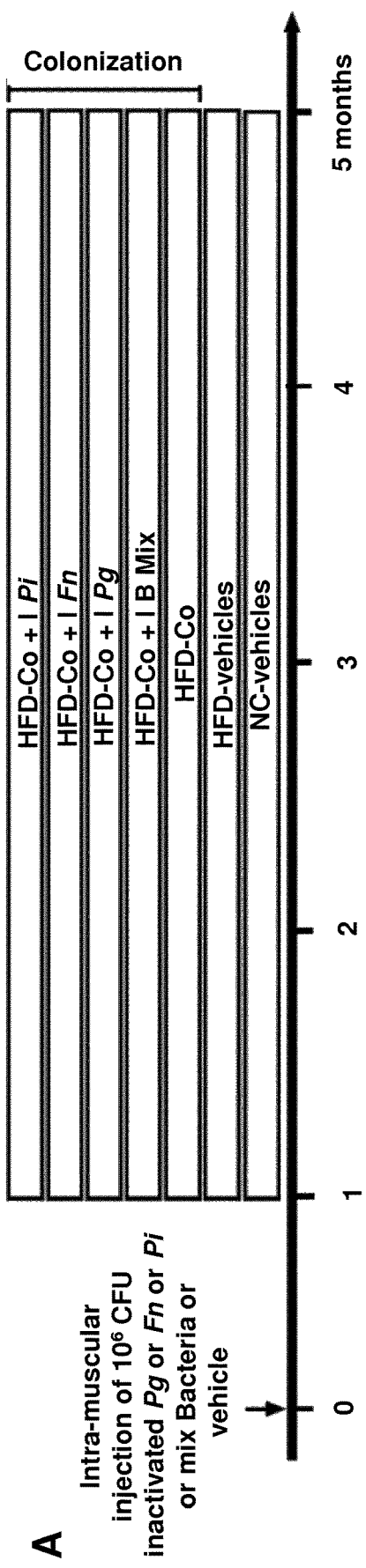
FIGURE 10 (beginning)

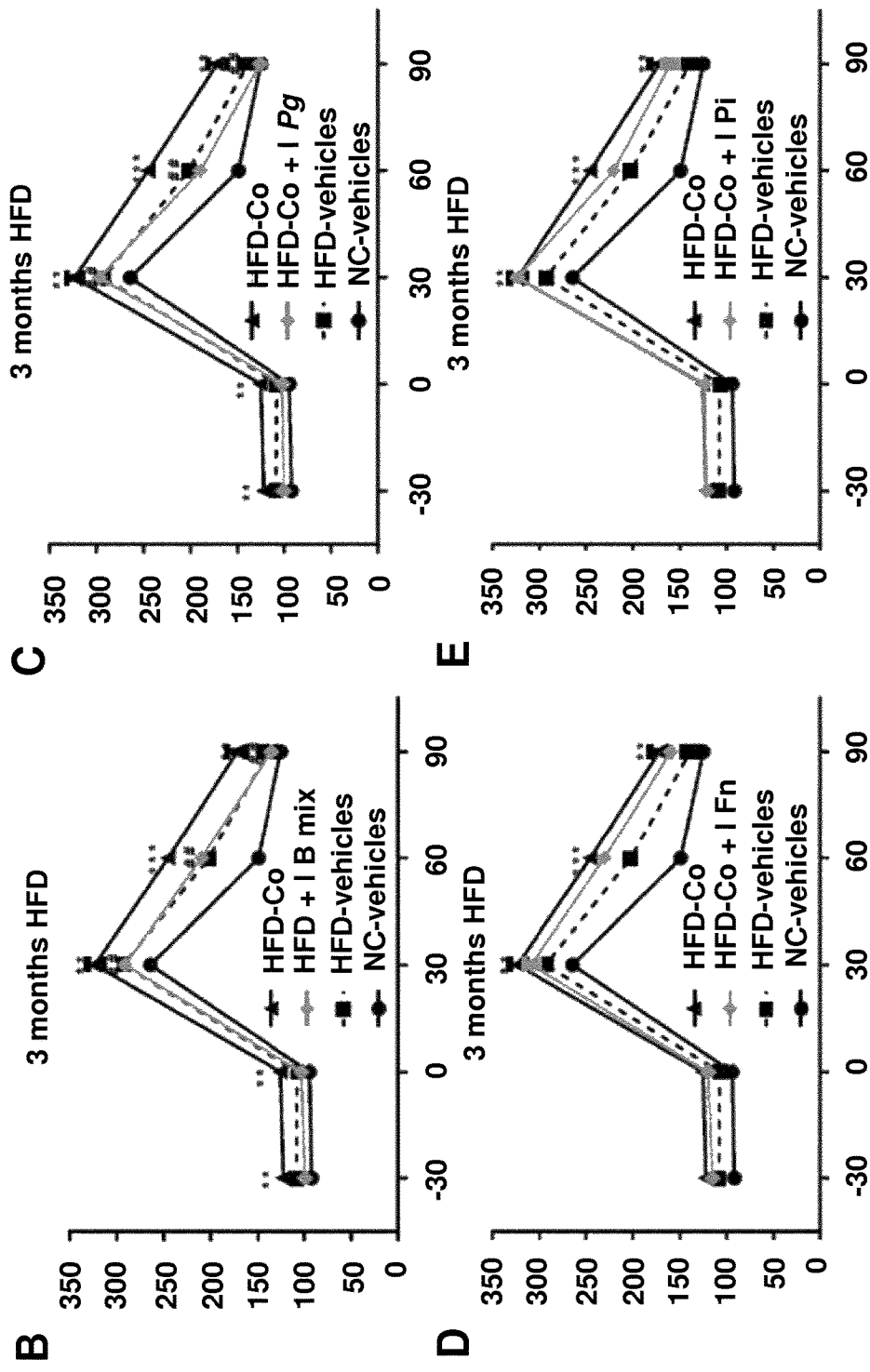
FIGURE 10 (continuing)

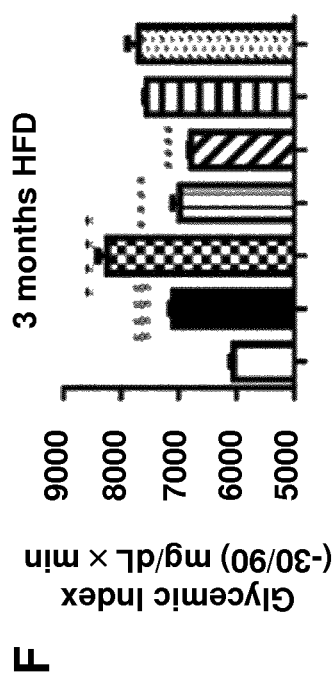
FIGURE 10 (end)

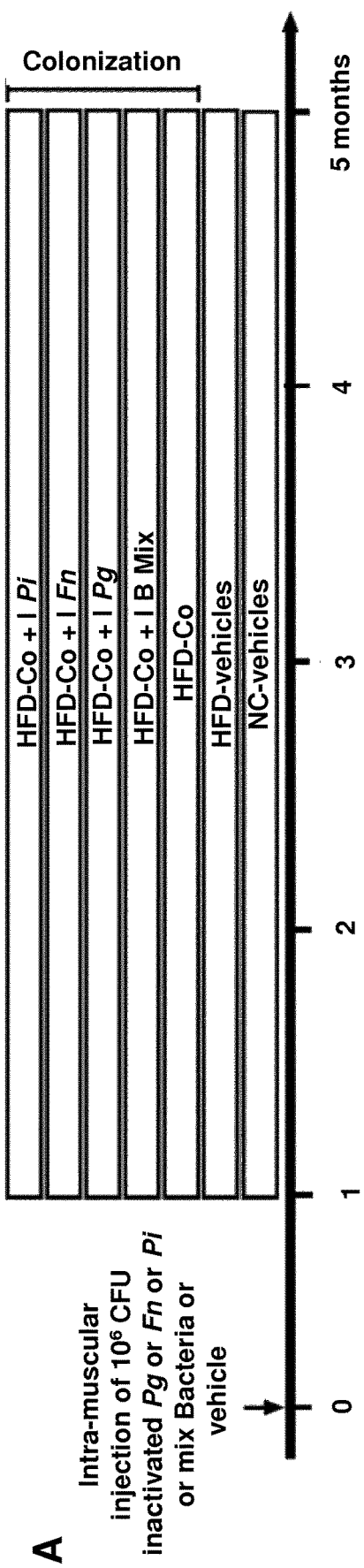
FIGURE 11 (beginning)

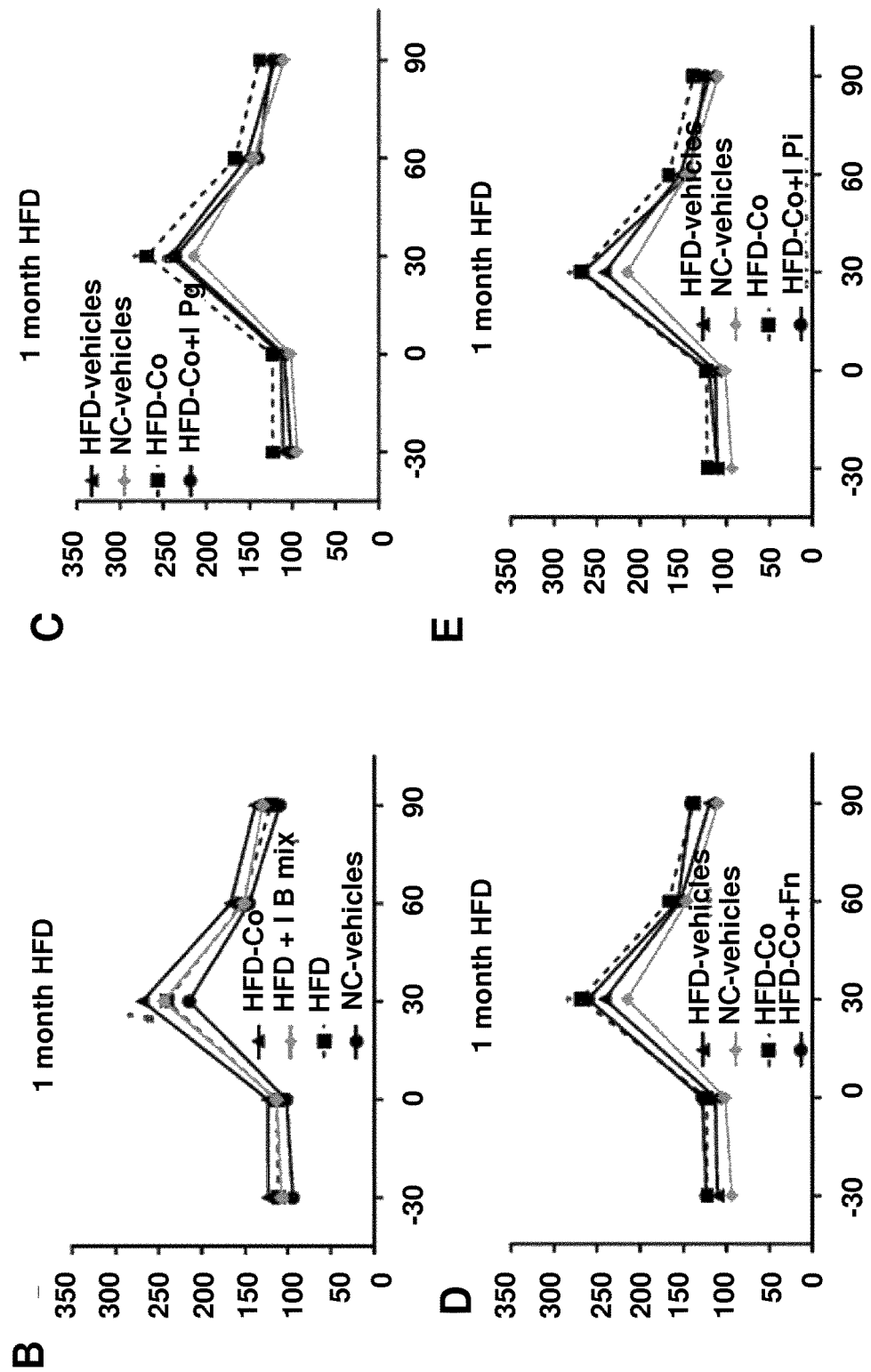
FIGURE 11 (continuing)

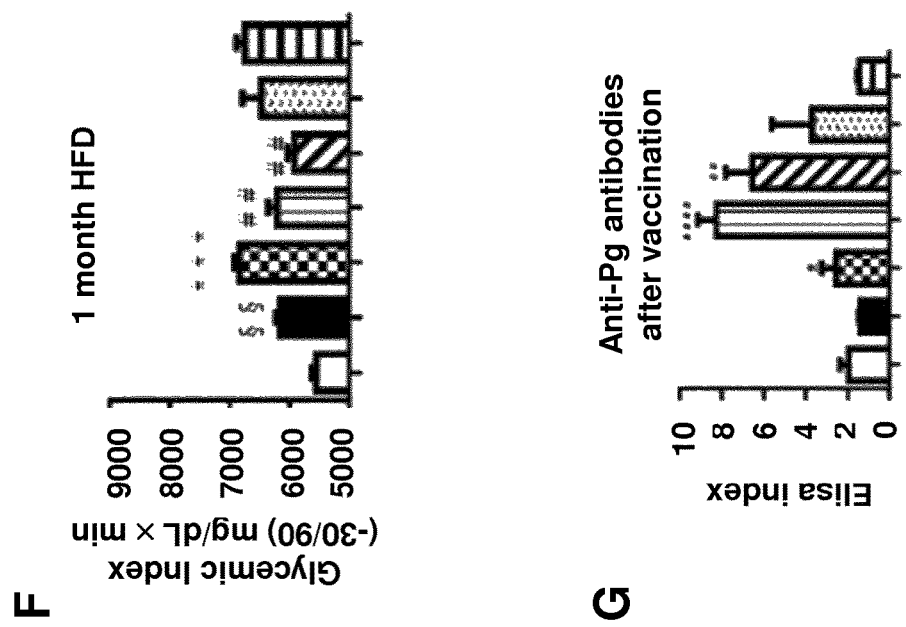
FIGURE 11 (end)

VACCINATION AGAINST DIABETES, OBESITY AND COMPLICATIONS THEREOF

The present invention concerns vaccination methods for preventing or treating diabetes, obesity and complications thereof.

Metabolic diseases, such as diabetes, overweight and obesity, both in developed and emerging countries have reached epidemic proportions. The causal origin of this accelerating development is related to several interacting factors such as sedentary lifestyle, excessive body weight, stress and bad feeding habits. Markedly, the prevalence of periodontitis within the diabetic population is 60% while it ranges from 20% to 50% in the general population. In patients with periodontal diseases the incidence of pre-diabetes or undiagnosed type 2 diabetes (T2D) is increased by 27-53%. Nonetheless, the causal link between periodontitis and T2D is still unknown.

Due to the deleterious impact of these metabolic diseases and their cardiometabolic and hepatic complications in human health, there is a need to develop vaccination strategies for these diseases and complications.

The present inventors hypothesized that a periodontal microbiota dysbiosis could initiate first a regional and then a systemic metabolic inflammation promoting obesity, insulin-resistance, T2D, and complications thereof. To demonstrate the causal role of periodontal diseases as a risk factor for T2D and the relevance of the innate and adaptive immune responses, the inventors have set up a unique and specific model of periodontitis by Gram-negative bacterial periodontal-pathogen colonization in mice.

They demonstrated on this model the causal role of the lack of regional adaptive immune system response against *Porphyromonas gingivalis* in the worsening of insulin-resistance and glycemic control induced by periodontitis.

They further showed that killed (or inactivated) *Porphyromonas gingivalis* could be used as a vaccine to reduce the impact of periodontitis on glucose metabolism, and therefore to prevent and treat diabetes, obesity and/or cardiometabolic and/or hepatic complications thereof in a subject.

The present invention thus concerns a composition comprising at least one prophylactically or therapeutically active agent selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a cDNA from *Porphyromonas gingivalis*, for use as a vaccine for preventing or treating periodontitis, diabetes, obesity and/or complications thereof in a subject.

The present inventors further demonstrated that glucose-tolerance was improved in mice which were administered with immune cells from periodontitis-model mice when compared to those which were administered with immune cells from healthy mice.

The present invention thus also concerns an isolated antibody having specificity for *Porphyromonas gingivalis* for use for preventing or treating periodontitis, diabetes, obesity and/or complications thereof in a subject.

DETAILED DESCRIPTION OF THE INVENTION

Periodontitis, Diabetes, Obesity and Complications Thereof

As used herein, the term "periodontitis" or "periodontal disease" refers to an inflammatory disease affecting the periodontium, i.e., the tissues that surround and support the teeth, and which involves progressive loss of the alveolar bone around the teeth.

As used herein, the term "diabetes" denotes a syndrome of disordered metabolism, usually due to a combination of hereditary and environmental causes, resulting in a concentration of glucose in plasma superior to 7 mmol/L. The term "diabetes" includes type 1 diabetes, type 2 diabetes, gestational diabetes and other states that cause hyperglycaemia.

Type 1 diabetes, also called insulin-dependent diabetes mellitus (IDDM) and juvenile-onset diabetes, is caused by β-cell destruction, usually leading to absolute insulin deficiency. Type 2 diabetes, also known as non-insulin-dependent diabetes mellitus (NIDDM) and adult-onset diabetes, is associated with predominant insulin resistance and thus relative insulin deficiency and/or a predominantly insulin secretory defect (or insulinopenia) with insulin resistance.

Preferably, the diabetes to be prevented in the context of the invention is type 2 diabetes.

As used herein, the term "obesity" refers to a medical condition in which excess body fat has accumulated to the extent that it may have an adverse effect on health, leading to reduced life expectancy and/or increased health problems. Obesity is typically determined by assessing the body mass index (BMI), a measurement which associates weight and height. In particular, people are defined as overweight if their BMI is between 25 $kg/m^2$ and 30 $kg/m^2$, and obese when it is greater than 30 $kg/m^2$.

As used herein, the term "complications of diabetes and/or obesity" includes cardiometabolic complications, hepatic complications, respiratory complications, renal complications, nervous system complications and inflammation complications.

As used herein, the term "cardiometabolic complication of diabetes and/or obesity" encompasses cardiovascular and metabolic complications of diabetes and/or obesity.

In a preferred embodiment, the cardiometabolic complications of diabetes and/or obesity to be prevented in the context of the invention are metabolic complications of diabetes and/or obesity. Metabolic complications of diabetes and/or obesity are well-known from the skilled person. Metabolic complications of obesity include insulin resistance, hyperinsulinemia, diabetes, in particular type 2 diabetes, and dyslipidemia. Metabolic complications of diabetes include diabetic ketoacidosis, hyperosmolar non-ketotic coma, lactic acidosis, hypoglycemia and dyslipidemia.

In another preferred embodiment, the cardiometabolic complications of diabetes and/or obesity to be prevented in the context of the invention are cardiovascular complications of diabetes and/or obesity.

Cardiovascular complications of diabetes and/or obesity are well-known from the skilled person. Cardiovascular complications of obesity include hypertension, cardiovascular disease (CVD), coronary artery disease, coronary heart disease (CHD), atherosclerosis, in particular iliac or femoral atherosclerosis, microangiopathy, angina pectoris, thrombosis, heart failure, stroke, vascular aneurysm, vascular calcification, acute coronary syndromes such as myocardial infarction, vascular stenosis and infarction, vascular dementia and brain ischemia. Cardiovascular complications of diabetes include hypertension, cardiovascular disease (CVD) and brain ischemia. Preferably, the cardiovascular complication of diabetes and/or obesity to be prevented or treated is selected from the group consisting of heart failure, atherosclerosis and brain ischemia.

As used herein, the expression "hepatic complication of diabetes and/or obesity" refers to any complication associated with diabetes and/or obesity which affects the liver. Hepatic complications of obesity are well-known from the skilled person and include hepatic steatosis, non-alcoholic steatohepatitis (NASH), liver fibrosis, cirrhosis and hepatocarcinoma. Hepatic complications of diabetes are well-known from the skilled person and include fatty liver, hepatic steatosis, liver fibrosis, cirrhosis and hepatocarcinoma. Preferably, the hepatic complication of diabetes and/or obesity to be prevented or treated is selected from the group consisting of NASH, liver fibrosis and cirrhosis.

As used herein, the expression "respiratory complications of diabetes and/or obesity" refers to any complication associated with diabetes and/or obesity which affects the respiratory airways. Such complications are well-known from the skilled person and include respiratory failure.

As used herein, the expression "renal complications of diabetes and/or obesity" refers to any complication associated with diabetes and/or obesity which affects kidneys. Such complications are well-known from the skilled person and include kidney failure.

As used herein, the expression "nervous system complications of diabetes and/or obesity" refers to any complication associated with diabetes and/or obesity which affects the central or peripheric nervous system, in particular which affects nervous cells. Such complications are well-known from the skilled person and include neuropathy and neurodegenerative diseases.

As used herein, the expression "inflammation complications of diabetes and/or obesity" refers to any complication associated with diabetes and/or obesity which involves inflammation. Such complications are well-known from the skilled person and include arthritis.

Subject

In the context of the present invention, a "subject" denotes a human or non-human mammal, such as a rodent (rat, mouse, rabbit), a primate (chimpanzee), a feline (cat), or a canine (dog). Preferably, the subject is human or a dog. The subject according to the invention may be in particular a male or a female.

In a particular embodiment, the subject is at risk of metabolic disease.

In a particular embodiment, the subject suffers from overweight, hypertension and/or high fasting blood glucose.

As used herein, the term "overweight" refers to an excess of body weight compared to set standards. The excess weight may come from muscle, bone, fat and/or body water. The US National Institutes of Health (NIH) identifies overweight as a BMI of 25-30 kg/m$^2$.

As used herein, the term "hypertension" refers to a medical condition in which the blood pressure is chronically elevated. In the context of the invention, hypertension is preferably defined by systolic/diastolic blood pressure of at least 140/90 mmHg or being on antihypertensive medication.

As used herein, the term "high fasting blood glucose" or "high fasting glycemia" refers to a syndrome of disordered metabolism, resulting in a glycemia, in particular a fasting glycemia, of more than 6.1 mmol/L.

In a particular embodiment, the subject is under high fat diet.

By "high fat diet" is meant a dietary consumption which contains greater than 20% of its total calories from fat. In some embodiments, the dietary consumption contains greater than 30% of its total calories from fat. In other embodiments, the dietary consumption contains greater than 40% of its total calories from fat.

In another particular embodiment, the subject suffers from periodontitis.

Vaccine

The present invention concerns a composition comprising at least one prophylactically or therapeutically active agent selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a cDNA from *Porphyromonas gingivalis*, for use as a vaccine for preventing or treating periodontitis, diabetes, obesity and/or complications thereof, as defined above, in a subject, as defined above.

In the context of the invention, the term "vaccine" encompasses both prophylactic vaccines and therapeutic vaccines. In a preferred embodiment, said vaccine is a prophylactic vaccine.

As well-known from the skilled person, *Porphyromonas gingivalis* belongs to the phylum Bacteroidetes and is a nonmotile, Gram-negative, rod-shaped, anaerobic, pathogenic bacterium.

A "prophylactically or therapeutically active agent" as used herein refers to any compound of a bacterium liable to induce an immune response against an infection by said bacterium. Said prophylactically or therapeutically active agent is selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a cDNA from *Porphyromonas gingivalis*.

Attenuated *Porphyromonas gingivalis* may typically be obtained by weakening a strain by stable mutations that allow the bacteria to infect humans only transiently.

Inactivated *Porphyromonas gingivalis* (or killed *Porphyromonas gingivalis*) may typically be obtained by oxygen-exposition of *Porphyromonas gingivalis* during 48 hours.

Preferably, said prophylactically or therapeutically active agent is attenuated or inactivated *Porphyromonas gingivalis*. More preferably, said prophylactically or therapeutically active agent is inactivated *Porphyromonas gingivalis*.

The composition used as a vaccine in the context of the invention may further comprise:
- at least one additional prophylactically or therapeutically active agent selected from the group consisting of live attenuated *Fusobacterium nucleatum*, killed or inactivated *Fusobacterium nucleatum*, a subunit of *Fusobacterium nucleatum*, a recombinant or isolated immunogenic polypeptide or peptide from *Fusobacterium nucleatum* or a cDNA from *Fusobacterium nucleatum*; and/or
- at least one additional prophylactically or therapeutically active agent selected from the group consisting of live attenuated *Prevotella intermedia*, killed or inactivated *Prevotella intermedia*, a subunit of *Prevotella intermedia*, a recombinant or isolated immunogenic polypeptide or peptide from *Prevotella intermedia* or a cDNA from *Prevotella intermedia*.

As well-known from the skilled person, *Fusobacterium nucleatum* belongs to the Fusobacteria phylum, and is an oral bacterium, indigenous to the human oral cavity, that plays a role in periodontal disease.

As well-known from the skilled person, *Prevotella intermedia* (formerly *Bacteroides intermedius*) is a Gram-negative, obligate anaerobic pathogenic bacterium involved in periodontal infections, belonging to the phylum Bacteroidetes.

Preferably, the composition used as a vaccine in the context of the invention may further comprise:
- at least attenuated *Fusobacterium nucleatum* or inactivated *Fusobacterium nucleatum*, preferably inactivated *Fusobacterium nucleatum*; and/or
- at least attenuated *Prevotella intermedia* or inactivated *Prevotella intermedia*, preferably inactivated *Prevotella intermedia*.

The composition used as a vaccine in the context of the invention may further comprise an adjuvant.

However, the inventors demonstrated that a strong prevention of diabetes, obesity and/or cardiometabolic and/or hepatic complications thereof could be obtained without any adjuvant. Accordingly, in a preferred embodiment, the composition does not include any adjuvant.

Antibody Having Specificity for *Porphyromonas gingivalis*

The present invention also concerns an isolated antibody having specificity for *Porphyromonas gingivalis* for use for preventing or treating periodontitis, diabetes, obesity and/or complications thereof, as defined above, in a subject, as defined above.

According to the present invention, the term "antibody" refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region.

Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al (Sequences of Proteins of Immunological Interest (National Institutes of Health, Bethesda, Md., 1991). As used herein, a "human framework region" is a framework region that is substantially identical (about 85%, or more, in particular 90%, 95%, or 100%) to the framework region of a naturally occurring human antibody.

The term "monoclonal antibody" or "mAb" as used herein refers to an antibody molecule of a single amino acid composition, that is directed against a specific antigen and that is produced by a single clone of B cells or hybridoma.

The term "chimeric antibody" refers to an engineered antibody which comprises a VH domain and a VL domain of an antibody derived from a non-human animal, a CH domain and a CL domain of another antibody, in particular a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

"Antibody fragments" comprise a portion of an intact antibody, preferably the antigen binding or variable region of the intact antibody. Examples of antibody fragments include Fv, Fab, F(ab')$_2$, Fab', dsFv, scFv, sc(Fv)$_2$, diabodies and multispecific antibodies formed from antibody fragments.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')$_2$.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

"dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. the antibody fragment of the invention), that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present.

The term "specific", when it refers to recognition of an antibody or binding of an antibody to a target, means that the antibody interacts with the target without interacting substantially with another target which does not structurally resemble the target. "Specific" recognition of *Porphyromonas gingivalis* means that the antibody is able to bind any antigen from *Porphyromonas gingivalis*, but is unable to bind an antigen from another bacterium.

Antibodies of the invention may be produced by any technique known in the art, such as, without limitation, any chemical, biological, genetic or enzymatic technique, either alone or in combination.

In the context of the invention, the antibody having specificity for *Porphyromonas gingivalis* may be used in combination with at least one isolated antibody having specificity for *Fusobacterium nucleatum* and/or at least one isolated antibody having specificity for *Prevotella intermedia*.

Medical Indication

The present invention further concerns a method for preventing or treating periodontitis, diabetes, obesity and/or complications thereof, as defined above, in a subject, as defined above, said method comprising administering a prophylactically or therapeutically effective amount of a vaccine composition comprising at least one prophylactically or therapeutically active agent selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a cDNA from *Porphyromonas gingivalis*, as defined above, in a subject in need thereof.

The present invention also concerns the use of a composition comprising at least one prophylactically or therapeutically active agent selected from the group consisting of attenuated *Porphyromonas gingivalis*, inactivated *Porphyromonas gingivalis*, a subunit of *Porphyromonas gingivalis*, a recombinant or isolated immunogenic polypeptide or peptide from *Porphyromonas gingivalis* or a cDNA from *Porphyromonas gingivalis*, as defined above, for the manufacture of a vaccine intended for the prevention or the treatment of periodontitis, diabetes, obesity and/or complications thereof, as defined above.

The present invention also concerns a method for preventing or treating periodontitis, diabetes, obesity and/or complications thereof, as defined above, in a subject, as defined above, said method comprising administering a prophylactically or therapeutically effective amount of an isolated antibody having specificity for *Porphyromonas gingivalis* as defined above.

The invention further concerns the use of an isolated antibody having specificity for *Porphyromonas gingivalis* as defined above for the manufacture of a medicament intended for the prevention or treatment of periodontitis, diabetes, obesity and/or complications thereof, as defined above.

As used herein, the term "prevention" refers to any indicia of success in protecting a subject or patient (e.g. a subject or patient at risk of developing a disease or condition) from developing, contracting, or having a disease or condition, including preventing one or more symptoms of a disease or condition or diminishing the occurrence, severity, or duration of any symptoms of a disease or condition following administration of a vaccinal or pharmaceutical composition as described herein.

As used herein, the term "treatment" means reversing, alleviating or inhibiting the progress of the disorder or condition to which such term applies, or one or more symptoms of such disorder or condition.

As used herein, the expression "prophylactically effective amount" means an amount of a composition that, when administered to a subject, will have the intended prophylactic effect, e.g., preventing or delaying the onset (or reoccurrence) of a disease, or reducing the likelihood of the onset (or reoccurrence) of a disease, or its symptoms. The full prophylactic effect does not necessarily occur by administration of one dose, and may occur only after administration of a series of doses (e.g. prime-boost). Thus, a prophylactically effective amount may be administered in one or more administrations. The exact amounts will depend on the purpose of the treatment, and will be ascertainable by one skilled in the art using known techniques.

As used herein, the expression "therapeutically effective amount" means a sufficient amount of a compound to treat a specific disease, at a reasonable benefit/risk ratio applicable to any medical treatment. It will be understood, however, that the total daily usage of the compounds of the present invention will be decided by the attending physician within the scope of sound medical judgment. The specific therapeutically effective dose level for any particular subject will depend upon a variety of factors including the disorder being treating and the severity of the disorder, activity of the specific compounds employed, the specific combinations employed, the age, body weight, general health, sex and diet of the subject, the time of administration, route of administration, the duration of the treatment, drugs used in combination or coincidental with the specific compounds employed, and like factors well known in the medical arts.

The prophylactically or therapeutically active agents and antibodies of the invention may be combined with pharmaceutically acceptable excipients, and optionally sustained-release matrices, such as biodegradable polymers, to form pharmaceutical or vaccinal compositions.

The prophylactically or therapeutically active agents and antibodies of the invention may be used in combination with other therapies against periodontitis, diabetes, obesity and/or complications thereof, in particular in combination with other therapies against diabetes and/or obesity.

Such therapies are well-known from the skilled person and include metformin, sulfonylureas, meglitinides, thiazolidinediones, DPP-4 inhibitors, GLP-1 receptor antagonists, SGLT2 inhibitors, insulin therapy, beta-methyl-phenylethylamine, orlistat, phentermine and sibutramine.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical or vaccinal compositions, the route of administration, the dosage and the regimen naturally depend upon the condition to be treated or prevented, the severity of the illness, the age, weight, and sex of the patient, etc.

The pharmaceutical or vaccinal compositions of the invention can be formulated for a topical, oral, parenteral, intranasal, intravenous, intramuscular, subcutaneous or intraocular administration, an administration in a gum or an administration in a tooth and the like.

Preferably, the vaccinal composition of the invention, as defined in the section "Vaccine" above is administered in a gum or tooth of the subject to be treated.

Preferably, the vaccinal compositions and antibodies of the invention are used for preventing or treating diabetes, obesity, and/or complications thereof, in particular cardiometabolic and/or hepatic complications thereof.

The vaccinal compositions and antibodies of the invention are particularly useful for preventing or treating complications of diabetes and/or obesity, in particular cardiometabolic and/or hepatic complications of diabetes and/or obesity in a subject, when said subject suffers from diabetes, in particular type 2 diabetes, and/or obesity.

They are also useful for reducing the effect of a comorbidity on worsening of diabetes and/or obesity, in particular in a subject who suffers from diabetes, in particular type 2 diabetes, and/or obesity.

By "comorbidity" is meant herein a medical condition in a patient that causes, is caused by, or is otherwise related to another condition in the same patient.

Comorbidities of diabetes and/or obesity are well-known from the skilled person and include periodontitis and the complications mentioned above.

Preferably, said comorbidity is periodontitis.

The present invention will be further illustrated by the figures and examples below.

BRIEF DESCRIPTION OF THE FIGURES

FIG. 1A) Mice were colonized with *Porphyromonas gingivalis* (Pg), *Fusobacterium nucleatum* (Fn) and *Prevotella intermedia* (Pi) or by vehicle solution for one month and then randomized in four groups: NC (normal chow, n=6), NC-Co (normal chow colonized, n=6), HFD (high-fat diet, n=7) and HFD-Co (High-fat diet colonized, n=10);

FIG. 1B) Alveolar Bone loss (in mm) for each group;

FIG. 1C) TNF-α, PAI-1, IL1-β, and IL-6 expression in periodontal tissue. NC: white bar; NC-Co: grey bar; HFD: black bar, and HFD-Co: checkerboard bar.

FIG. 2) Histological examination for hemi-mandibles stained with hematolin/eosin, F4/80, CD3 and CD45 antibodies: cells count is shown for each group. NC: white bar; NC-Co: grey bar; HFD: black bar, and HFD-Co: checkerboard bar.

FIG. 3A) Number of immune cell-types explored at 3 months in cervical lymph-nodes of each group.

FIG. 3B) Relative abundance of immune cell-types explored at 3 months in cervical lymph-nodes of each group. NC: white bar; NC-Co: grey bar; HFD: black bar, and HFD-Co: checkerboard bar.

FIG. 4A) Number of immune cell-types explored at 3 months in spleen of each group.

FIG. 4B) Relative abundance of immune cell-types explored at 3 months in spleen of each group. NC: white bar; NC-Co: grey bar; HFD: black bar, and HFD-Co: checkerboard bar.

FIG. 5) Relative abundance of immune cell-types explored at 3 months in blood of each group. NC: white bar; NC-Co: grey bar; HFD: black bar, and HFD-Co: checkerboard bar. Data (mean±SEM) and One-way ANOVA followed by Tukey's test used for *$P<0.05$ and ****$P<0.0001$ when compared to HFD, $^§$ $P<0.05$; $^{§§}$ $P<0.001$ $^{§§§§}$ $P<0.0001$ when compared to NC and $^\$$$P<0.05$ when compared to NC-Co.

FIGS. 6-8. Periodontitis enhances HFD-induced metabolic disorders in mice.

FIG. 6A) Glycaemic profiles (mg/dL) during an Intraperitoneal Glucose-Tolerance Test (IpGTT NC (normal chow, white bar, n=6), NC-Co (normal chow colonized, grey bar, n=6), HFD (high-fat diet, black bar n=7) and HFD-Co (High-fat diet colonized, checkerboard bar, n=10) and glycaemic indexes as inset; for each group during 1 month.

FIG. 6B) Ratio fat/lean for each group during 1 month.

FIG. 6C) Glycaemic profiles (mg/dL) during an Intraperitoneal Glucose-Tolerance Test (IpGTT NC (normal chow, white bar, n=6), NC-Co (normal chow colonized, grey bar, n=6), HFD (high-fat diet, black bar n=7) and HFD-Co (High-fat diet colonized, checkerboard_bar, n=10) and glycaemic indexes as inset; for each group during 2 months.

FIG. 6D) Ratio fat/lean for each group during 2 months.

FIG. 6E) Glycaemic profiles (mg/dL) during an Intraperitoneal Glucose-Tolerance Test (IpGTT NC (normal chow, white bar, n=6), NC-Co (normal chow colonized, grey bar, n=6), HFD (high-fat diet, black bar n=7) and HFD-Co (High-fat diet colonized, checkerboard bar, n=10) and glycaemic indexes as inset; for each group during 3 months.

FIG. 6F) Ratio fat/lean for each group during 3 months.

FIG. 7) Insulin-sensitivity evaluated by the euglycaemic-hyperinsulinemic clamp technique.

FIG. 8) Correlation between Glucose Infusion Rate (GIR) and ABL (alveolar bone loss). Data are mean±SEM. Significant results when: *$P<0.05$; $P<0.01$ and *$P<0.001$ when compared to HFD, $^§$ $P<0.05$ and $^{§§§}$ $P<0.001$ when compared to NC and $^\$$$P<0.05$ when compared to NC-Co as determined by Two-Way ANOVA with Bonferroni's post-test for FIG. A, C and E and one-way ANOVA followed by Tukey's post-test for FIG. 6B, D, F, and FIG. 7.

FIG. 9. Immune cells transfer from cervical lymph-nodes from periodontitis mice reduce colonization-induced glucose-intolerance.

FIG. 9A) Immune cells from cervical lymph-nodes from donor mice with or without periodontitis were transferred to recipient mice. Then, each group was colonized by Pg, Fn and Pi in periodontal tissue for four weeks.

FIG. 9B) Intra-peritoneal glucose-tolerance tests were performed in recipient mice after transfer (not shown) and after colonization.

FIG. 9C) Glycaemic index. PTC+NC-Co: Periodontitis transfer+Colonization; HTC+NC-Co: Healthy transfer+Colonization; PCT+NC: Periodontitis transfer without colonization; HTC+NC: Healthy transfer without colonization. Data are mean±SEM. Significant results when: ***$P<0.001$ when compared to HTC+NC as determined by one-way ANOVA followed by Tukey's test (C) and Two-Way ANOVA with Bonferroni's post-test (B).

FIG. 10. Pre-treatment with inactivated *Porphyromonas gingivalis* prevents periodontitis-aggravated glucose-intolerance in HFD-fed mice.

FIG. 10A) Mice were injected by $10^6$ CFU of inactivated *Porphyromonas gingivalis* or inactivated *Fusobacterium nucleatum* or inactivated *Prevotella intermedia* or a mix of all inactivated bacteria or vehicle solution. 1 month later, mice were colonized by Pg, Fn, Pi and or by vehicle solution for one month and then randomized in 7 groups: NC-vehicles (vehicle+normal chow, n=4), HFD-vehicles (vehicle+HFD, n=4), HFD-Co (vehicle+HFD+colonization, n=4), HFD-Co+I B mix (inactivated mix bacteria+colonization+HFD, n=4), HFD-Co+I Pg (inactivated *Porphyromonas gingivalis*+colonization+HFD, n=4), HFD-Co+I Fn (inactivated *Fusobacterium nucleatum*+colonization+HFD, n=4) and HFD-Co+I Pi (inactivated *Prevotella intermedia*+colonization+HFD, n=4).

FIG. 10B-E) Intraperitoneal Glucose-Tolerance Test (Ip-GTT) was assessed for each group after 3 months of HFD.

FIG. 10F) Glycaemic index was assessed for each group after 3 months of HFD. NC-vehicles: white bar, HFD-vehicles: black bar, HFD-Co: checkerboard bar, HFD-Co+I B mix: vertical striped bar, HFD-Co+I Pg: diagonal striped bar, HFD-Co+I Fn: horizontal striped bar, HFD-Co+I Pi: grey pointed bar.

FIG. 10G) Measurement of Immunoglobulin G antibodies specific to LPS of *Porphyromonas gingivalis* in blood. NC-vehicles: white bar, HFD-vehicles: black bar, HFD-Co: checkerboard bar, HFD-Co+I B mix: vertical striped bar, HFD-Co+I Pg: diagonal striped bar, HFD-Co+I Fn: horizontal striped bar, HFD-Co+I Pi: grey pointed bar.

FIG. 10H) Alveolar Bone loss was explored after experimental procedures for each group. NC-vehicles: white bar, HFD-vehicles: black bar, HFD-Co: checkerboard bar, HFD-Co+I B mix: vertical striped bar, HFD-Co+I Pg: diagonal striped bar, HFD-Co+I Fn: horizontal striped bar, HFD-Co+I Pi: grey pointed bar.

Figure 1:
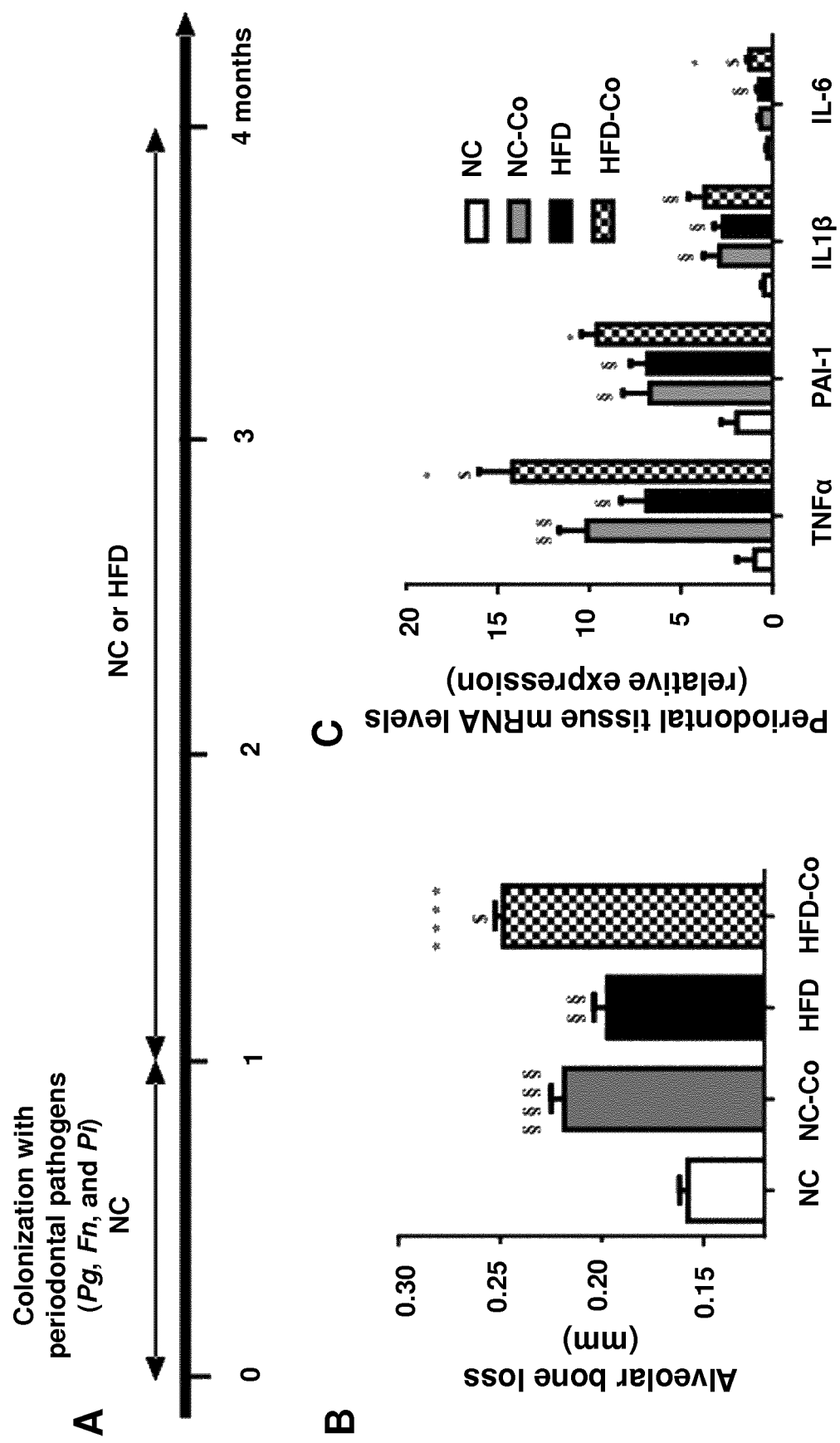
FIGS. 1-5. Oral colonization with Pg, Fn and Pi induces periodontitis associated with local and systemic immune disorders.

Data are mean±SEM. Significant results when: $P<0.01$, *$P<0.001$ and ****$P<0.0001$ when compared to HFD-vehicles, § $P<0.05$ and §§§§ $P<0.0001$ when compared to NC-vehicles and #$P<0.05$ and ####$P<0.0001$ when compared to HFD-Co as determined by Two-Way ANOVA with Bonferroni's post-test for B, C, D and E and one-way ANOVA followed by Tukey's post-test for F and G.

FIG. 11. Pre-treatment with inactivated *Porphyromonas gingivalis* induced production of antibodies against *Porphyromonas gingivalis*

FIG. 11A) Mice were injected by $10^6$ CFU of inactivated *Porphyromonas gingivalis* or inactivated *Fusobacterium nucleatum* or inactivated *Prevotella intermedia* or a mix of all inactivated bacteria or vehicle solution. 1 month later, mice were colonized by Pg, Fn, Pi and or by vehicle solution for one month and then randomized in 7 groups: Sham (vehicle+normal chow, n=4), HFD (vehicle+HFD, n=4), HFD-Co (vehicle+HFD+colonization, n=4), HFD-Co+I B mix (inactivated mix bacteria+colonization+HFD, n=4), HFD-Co+I Pg (inactivated *Porphyromonas gingivalis*+colonization+HFD, n=4), HFD-Co+I Fn (inactivated *Fusobacterium nucleatum*+colonization+HFD, n=4) and HFD-Co+ inactivated Pi (inactivated *Prevotella intermedia*+colonization+HFD, n=4).

FIG. 11B-E) Intraperitoneal Glucose-Tolerance Test (Ip-GTT) was assessed for each group after 1 month of HFD.

FIG. 11F) Glycaemic index was assessed for each group after 1 month of HFD. NC-vehicles: white bar, HFD-vehicles: black bar, HFD-Co: checkerboard bar, HFD-Co+I B mix: vertical striped bar, HFD-Co+I Pg: diagonal striped bar, HFD-Co+I Fn: grey pointed bar, HFD-Co+I Pi: horizontal striped bar.

FIG. 11G) Measurement of Immunoglobulin G antibodies specific to LPS of *Porphyromonas gingivalis* in blood. NC-vehicles: white bar, HFD-vehicles: black bar, HFD-Co: checkerboard bar, HFD-Co+I B mix: vertical striped bar, HFD-Co+I Pg: diagonal striped bar, HFD-Co+I Fn: grey pointed bar, HFD-Co+I Pi: horizontal striped bar. Data are mean±SEM. Significant results when: $P<0.01$, *$P<0.001$ and ****$P<0.0001$ when compared to HFD-vehicles, § $P<0.05$ and §§§§ $P<0.0001$ when compared to NC-vehicles and #$P<0.05$ and ####$P<0.0001$ when compared to HFD-Co as determined by Two-Way ANOVA with Bonferroni's post-test for B, C, D and E and one-way ANOVA followed by Tukey's post-test for F and G.

EXAMPLES

Example 1: Design of a Mouse Model of Periodontitis

This example describes the production of a mouse model of periodontitis used by the inventors to design a vaccine for prevention of diabetes and obesity.

Material and Methods

Animals and Experimental Procedures.

C57Bl/6J wild-type (WT) (Charles River, L'Arbresle, France) female mice were group-housed (six mice per cage) in a specific pathogen-free controlled environment (inverted 12-hr daylight cycle, light off at 10:00 a.m.). Five week-old mice were randomized in 2 groups: group one was colonized (Co) and group two served as control. For group one, 1 ml of a mix of $10^9$ CFU of each periodonto-pathogen such as *Porphyromonas gingivalis* (Pg) ATCC 33277, *Fusobacterium nucleatum* (Fn) and *Prevotella intermedia* (Pi) in 2% carboxymethylcellulose was applied at the surface of the mandibular molar teeth, four times a week, during one month. Control mice received the vehicle only. Each group was divided in two subgroups and fed with either a normal chow (NC, energy content: 12% fat, 28% protein, and 60% carbohydrate; A04, Villemoisson-sur-Orge, France) or a diabetogenic, high-fat carbohydrate-free diet (HFD; energy content: 72% fat (corn oil and lard), 28% protein and less than 1% carbohydrate; SAFE, Augy, France) for 3 months. The groups were labelled as following: NC+vehicle (NC), NC+colonization (NC-Co), high-fat diet (HFD) and HFD+colonization (HFD-Co). All animal experimental procedures were approved by the local ethical committee of Rangueil University Hospital (Toulouse, France).

Quantification of Mandibular Alveolar Bone Resorption.

Hemi-mandibles were scanned using a high-resolution µCT (Viva CT40; Scanco Medical, Bassersdorf, Switzerland). Data were acquired at 45 keV, with a 10 µm isotropic voxel size. Six linear measurements were obtained from each molar by using a stereomicroscope with an on-screen computer-aided measurement package. The alveolar bone loss (mm) was measured from the cemento-enamel junction (CEJ) to the alveolar bone crest (ABC) for each molar. Three-dimensional reconstructions were generated from a set of 400 slices.

Real-Time Quantitative PCR (qPCR) Analysis for Periodontal Tissue.

Total RNA from periodontal tissue was extracted using the TriPure reagent (Roche, Basel, Switzerland). cDNA was synthesized using a reverse transcriptase (Applied Biosystems, Fost City, USA) from 1 µg of total RNA as described in Blasco-Baque et al. (2012) *PLoS One* 7:e48220. The primers (Eurogentec, San Diego, USA) used were (5' to 3'): tumor necrosis factor-α (TNF-α), forward TGGGACAGTGACCTGGACTGT (SEQ ID NO: 1); reverse TCGGAAAGCCCATTTGAGT (SEQ ID NO: 2); Interleukin 1β (IL-1β) forward TCGCTCAGGGT-CACAAGAAA (SEQ ID NO: 3); reverse CATCAGAGGCAAGGAGGAAAAC (SEQ ID NO: 4); plasminogen activator inhibitor-1 (PAI-1) forward ACAGCCTTTGTCATCTCAGCC (SEQ ID NO: 5); reverse CCGAACCACAAAGAGAAAGGA (SEQ ID NO: 6) and interleukin (IL-6) forward ACAAGTCGGAGGCTTAAT-TACACAT (SEQ ID NO: 7); reverse TTGCCAT-TGCACAACTCTTTTC (SEQ ID NO: 8). The concentration of each mRNA was normalized for RNA loading against the ribosomal protein L19 (RPL19) (forward GAAGGT-CAAAGGGAATGTGTTCA (SEQ ID NO: 9); reverse CCTTGTCTGCCTTCAGCTTGT (SEQ ID NO: 10)) as an internal standard and the data were analysed according to the $2^{-\Delta\Delta C_T}$ method, as described in Serino et al. (2011) *PLoS One* 6:e21184.

Intraperitoneal Glucose-Tolerance Test (IPGTT) and In Vivo Glucose Infusion Rate.

Six-hour fasted mice were injected with glucose into the peritoneal cavity (1 g/kg). Blood glucose was measured with a glucometer (Roche Diagnostics, Meylan, France) on 2 µl of blood collected from the tip of the tail vein at −30, 0, 30, 60 and 90 min after the glucose injection. To assess insulin-sensitivity, a catheter was indwelled into the femoral vein as described in Cani et al. (2007) *Diabetes* 56:1761-1772. After full recovery from the surgery and 6 hours of fasting, the whole body glucose utilization rate was evaluated in euglycemic/hyperinsulinemic conditions, as described in Cani et al. (2007) *Diabetes* 56:1761-1772.

Histological Analyses.

Hemi-Mandibles were excised, fixed in 4% paraformaldehyde for 48 hours and embedded in paraffin. Hemi-mandibles samples were cut with a microtome in the transverse direction following the main axis of tooth from coronal to apical. Then, sections (4 µm thickness), were stained with hematoxylin/eosin. Immunohistological analyses were performed using primary antibodies against F4/80 (AbD Serotec, Colmar, France), CD3 (Spring Bioscience, Pleasanton USA) and CD45R (Bio-Rad Laboratoires, Marnes-La-Coquette, France), and revealed by R.T.U. (Ready-to-Use) Vectastin® Elite (Vector Laboratories, Burlingame, USA) and for diaminobenzidine (DAB) by Imm-PACT™ DAB Substrate (Vector Laboratories, Burlingame, USA), to quantify the infiltration of immune cells. Slides were scanned with «panoramic digital scanner 250" with Z-Stack function and the objective 40× (3DHISTECH). The cells subpopulations counting was done with the Panoramic Viewer software (3DHISTECH) and was carried into the Lamina propria gingivae and periodontal ligament on average surface 127000 µm2 on each tissue section Five microscopic fields of 0.02 µm$^2$ were counted on each slide by two independent naïve investigators.

Surface Staining and Antibodies Treatment of Immune Cells from Cervical Lymph-Nodes, Spleen and Blood.

Mononuclear cell suspensions were incubated for 15 min with anti-CD16/32 to block Fc receptors and then with antibodies, anti-CD4 APC (RMA4-5, eBioscience), CD8 V450 (53.6.7, BD Bioscience), anti-CD11b APC-eFluor780 (M1/70, eBioscience), CD45 V500 (30F11, BD Bioscience), anti-CD19 FITC (1D3, BD Bioscience) anti-TCR PerCP-Cy5.5 (H57, eBioscience) for 30 min on ice. LIVE/DEAD Fixable Cell Stain Kit (Life technologies) was used to remove dead cells. All data were acquired using a digital flow cytometer (LSR II Fortessa, Becton Dickinson), and analyzed with FlowJo software (Tree Star).

Plasma Biochemical Assays.

50 µl of blood were sampled from the retro-orbital sinus in awake condition in six-hour-fasted mice. For insulin, the plasma was separated and frozen at −80° C. 10 µl of plasma were used to determine insulin concentration with an Elisa kit (Mercodia, Uppsala, Sweden) following the manufacturer's instructions. Plasma cytokines concentration was determined by the MILLIPLEX® MAP system (Luminex, Austin 12212 Technology Blvd. Austin, Tex. 78727 United States/Merck Millipore Headquarters 290 Concord Road Billerica, Mass. 01821).

Statistical Analysis.

Results are presented as mean values±SEM. One-way ANOVA followed by Tukey's post-test was used to assess inter-groups differences, except for the IPGTT, where two-way ANOVA followed by Bonferroni's post-test was applied. *$P<0.05$; $P<0.01$; *$P<0.001$ and ****$P<0.0001$ when compared to HFD, § $P<0.05$; §§ $P<0.001$ §§§ $P<0.0001$ when compared to NC and \$$P<0.05$ when compared to NC-Co defined statistical significance. Statistical analyses were performed using GraphPad Prism version 5.00 for Windows Vista (GraphPad Software, San Diego, Calif.).

Results

*Porphyromonas gingivalis* (Pg), *Fusobacterium nucleatum* (Fn) and *Prevotella intermedia* (Pi), periodontal pathogens, are drivers for the development of periodontitis in mice. Here, the inventors generated a unique mouse model. First, periodontitis was induced by colonizing five-week-old wild-type C57Bl6/J female mice with all three pathogens; then, mice were fed with a normal chow (NC) or a diabetogenic/not obesogenic high-fat diet (HFD) (FIG. 1A).

Figure 2:
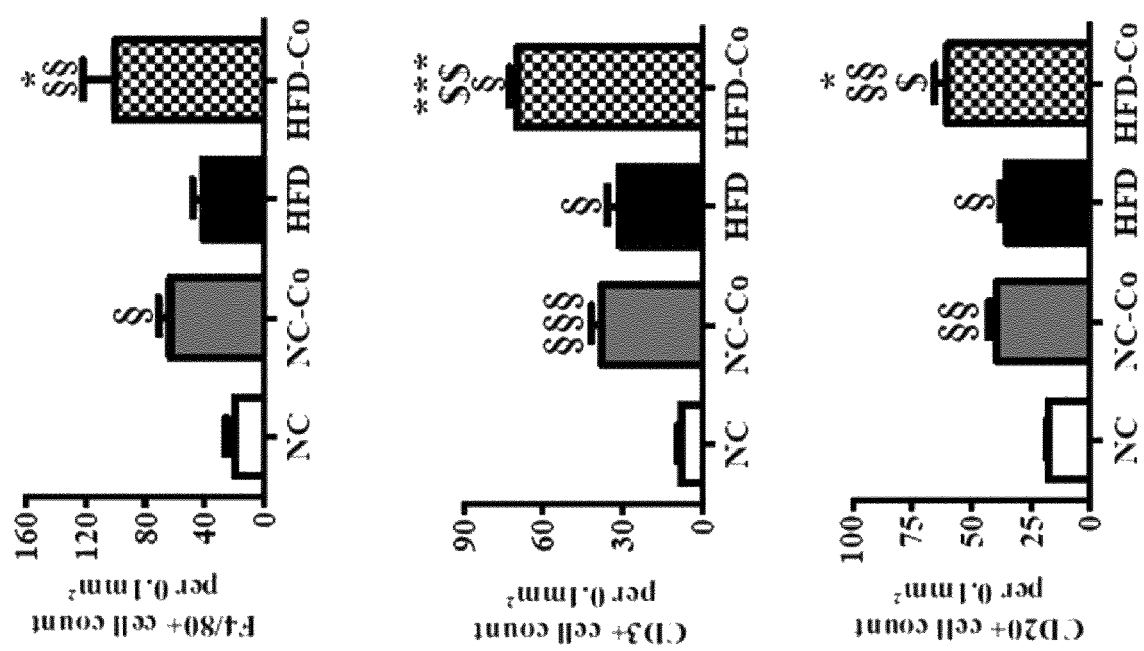

The inventors validated this model by showing periodontal pathogens-induced mandibular alveolar bone loss, a feature of periodontitis, on NC. Moreover, this parameter was worsened on HFD (FIG. 1B). Then, the inventors studied the periodontal tissue looking for a putative inflammatory status. As shown in FIG. 1C, NC-fed colonized mice displayed a significant increased gene expression for all the analysed cytokines. Moreover, the pro-inflammatory effect due to TNF-α and PAI-1 was increased by HFD (FIG. 1C). Subsequently, given this evidence, the inventors analysed histological sections of hemi-mandibles. They showed by hematoxylin/eosin staining that cells infiltrated the periodontal tissue (FIG. 2) after the colonization with the periodontal pathogens under normal chow. In addition, they characterized the cell-types by immunostaining and showed that an increased macrophages (cells F4/80+), lymphocytes T (cells CD3+) and lymphocytes B (cells CD45+) number in the same experimental conditions. In response to the HFD treatment, the number of cells increased when compared to NC-fed mice. Eventually, in colonized HFD-fed mice the number of immune cells even further increased over that of NC, NC-Co, and HFD mice, showing the impact of the dietary treatment and of the colonization on the inflammatory process in periodontal tissue (FIG. 2).

Next, to identify whether periodontitis and local inflammation may be associated with an impaired immune system, the inventors quantified local (cervical lymph-node) and systemic (spleen) adaptive and innate immune system cells. HFD-feeding increased the number of cells in both cervical lymph-node and spleen when compared to NC-fed mice.

Interestingly, periodontitis blunted this increase only in HFD-fed mice (FIGS. 3A and 4A).

In the latter, this variation was due to a strong reduction in the frequency of innate CD11b+ cells (gating on CD3-CD19-CD11c-CD11b+) in cervical lymph-nodes and spleen, whereas periodontitis increased the frequency of T and B lymphocytes (CD4+, CD8+ and CD19+) during HFD only (FIGS. 3B and 4B).

Figure 3:
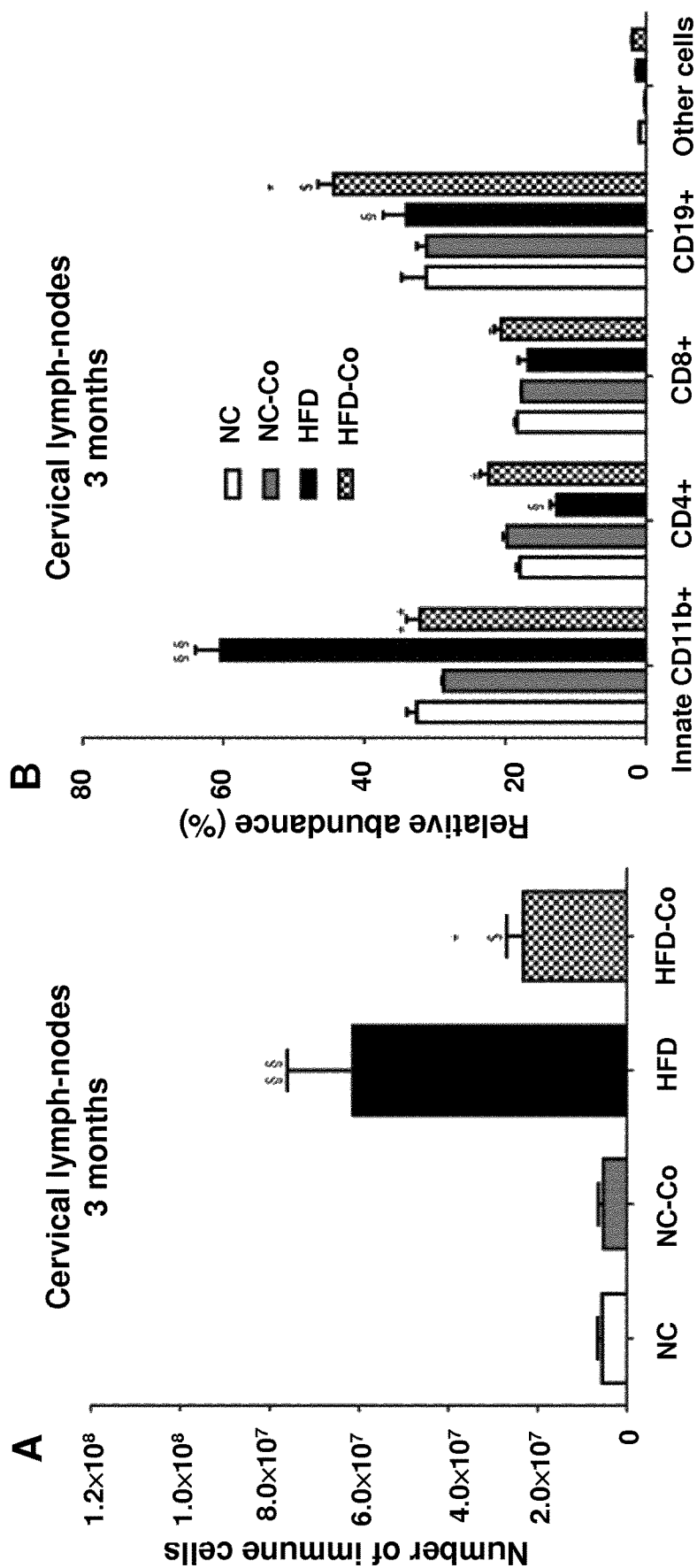
Figure 4:
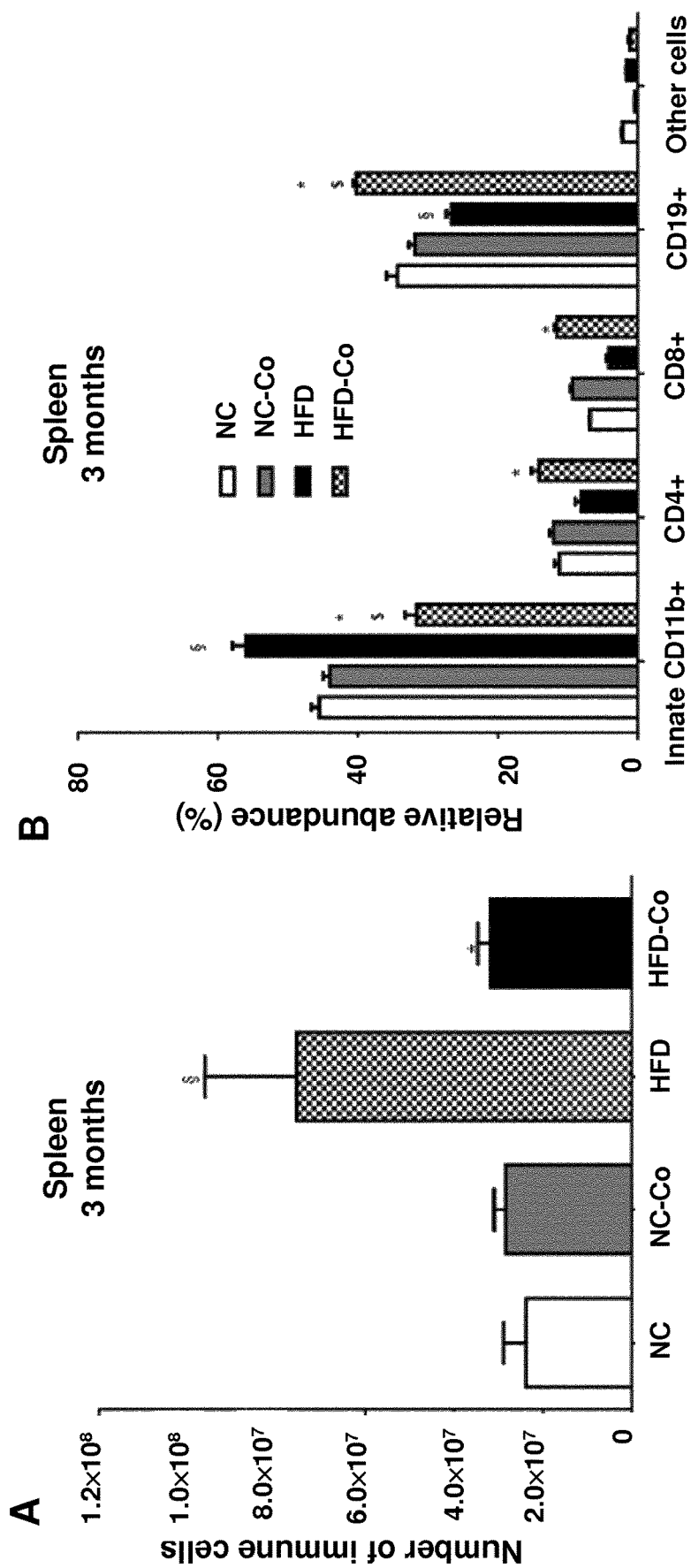
Figure 5:
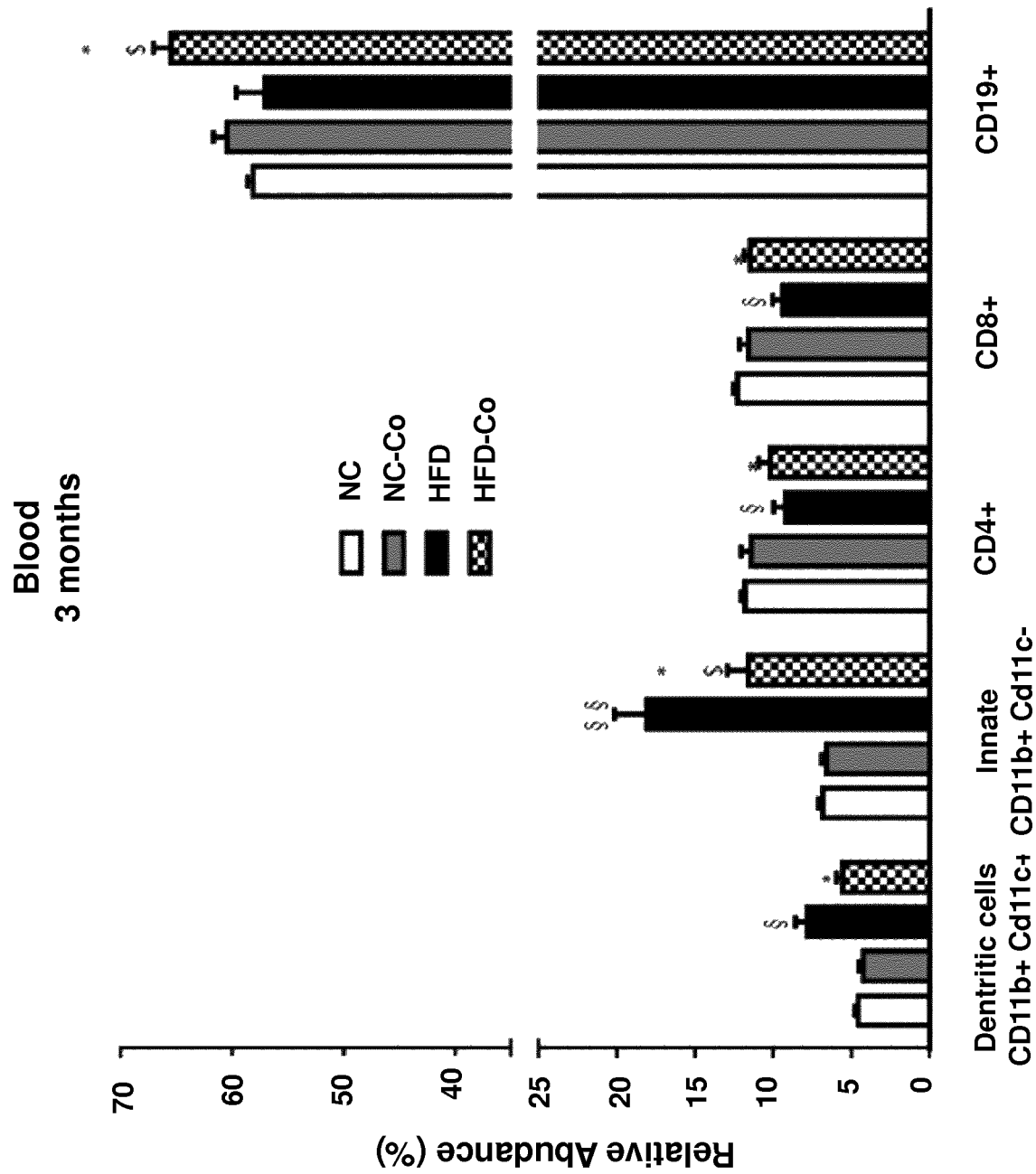
Figure 7:
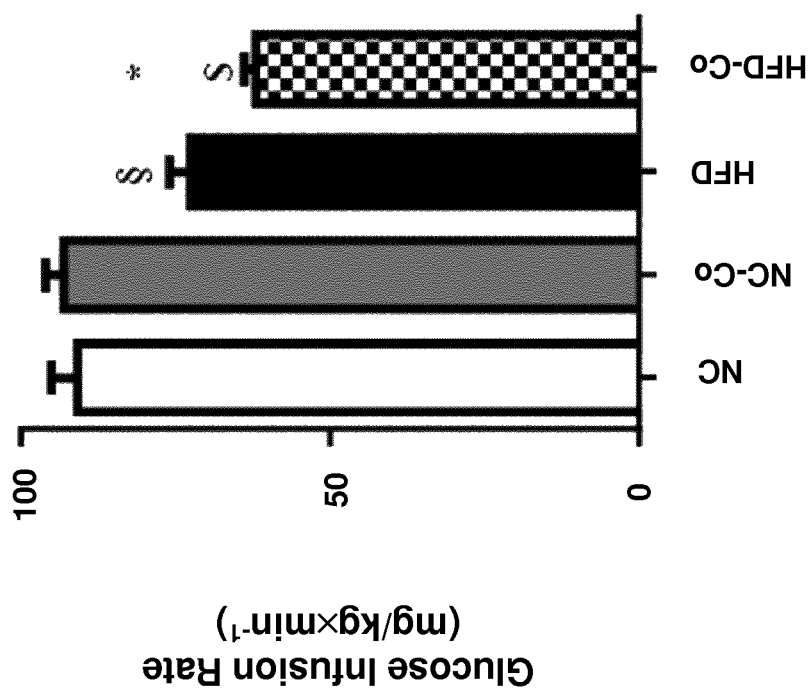
Figure 8:
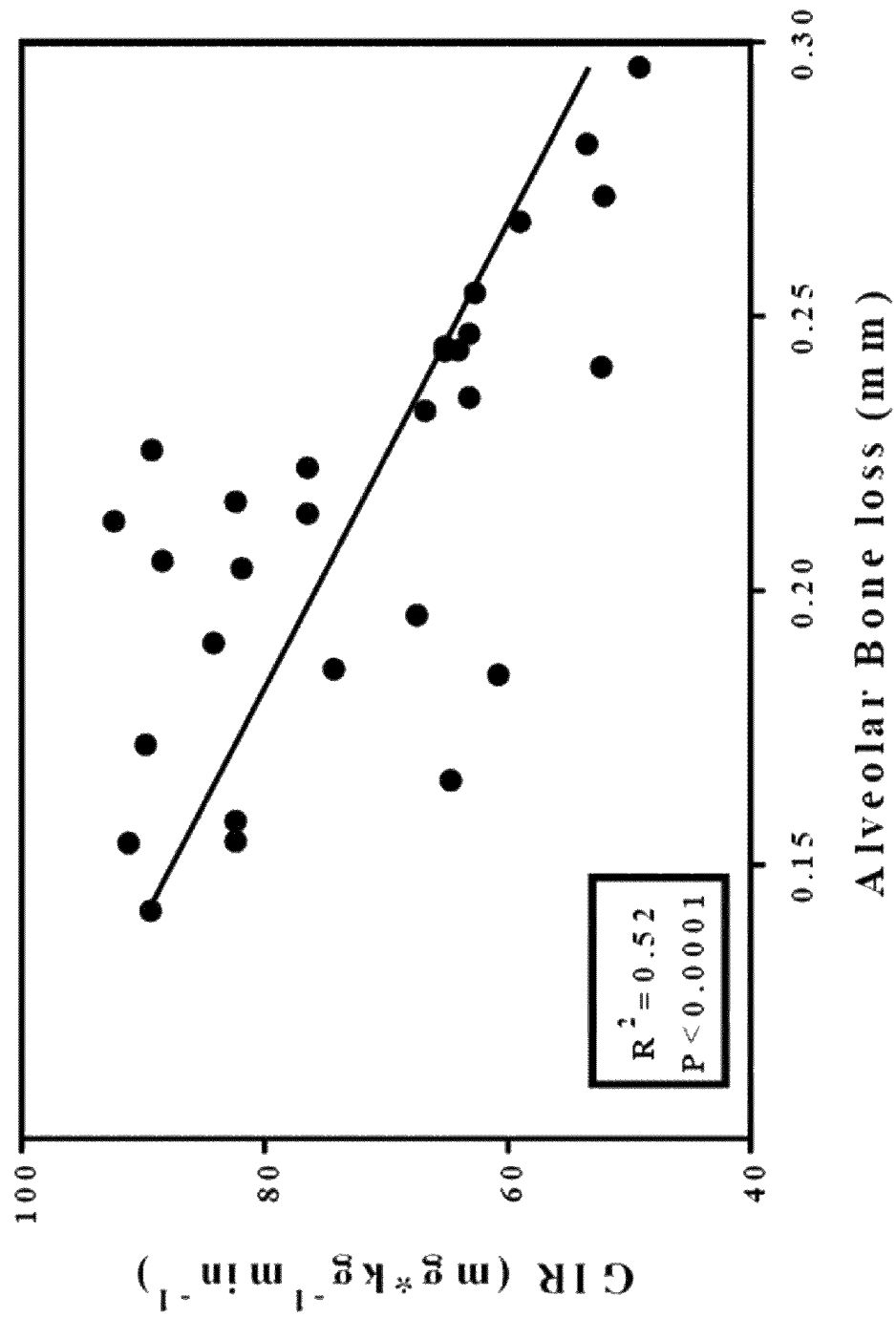

To further explore the systemic effect of periodontitis, the inventors analysed immune cells in blood, where the above reported modifications were confirmed for all cell types and especially for dendritic cells (CD11b+CD11c+) and Innate CD11b+CD11c− (FIG. 5). By contrast, periodontitis had no significant impact on any cell type whatever the tissue under normal chow (FIGS. 3-5). Indeed, the periodontal colonization increased the number of antibodies anti-PG on NC whereas the HFD treatment reduced IgG serum levels and antibodies anti-PG in colonized mice only (Table 1). Conversely, HFD increased IgG serum levels independently of colonization at both 2 and 3 months of treatment (Table 1). Moreover, the periodontitis increased blood IL-6 on HFD and decreased blood IFN-gamma concentrations on HFD and NC at 3 months (Table 1).

induced glucose-intolerance by the first and up to the third month of treatment (FIGS. 6A, C, E). These data were associated with a progressive and significant increase in the fat/lean mass ratio (FIGS. 6B, D, F). Furthermore, according to the time course, periodontitis increased plasma leptin and insulin concentrations on HFD at 3 months (Table 1). Insulin-resistance (indexed by the glucose-infusion rate (GIR)), as assessed by the euglycemic/hyperinsulinemic clamp technique, was induced by the periodontitis in HFD-fed mice only (FIG. 7). Importantly, alveolar bone loss was strongly and significantly correlated ($R^2=0.52$; $P<0.0001$) with insulin-resistance (FIG. 8).

Altogether, these data show that periodontitis aggravates HFD-induced glucose-intolerance and insulin-resistance.

Example 2: The Transfer of Cervical Lymph-Node Cells from Mice Models of Periodontitis to Naïve Recipients Guards Against Periodontitis-Aggravated Metabolic Disease Materials and Methods
Animals and Experimental Procedures.
See example 1.

TABLE 1

| Param. | NC | | | NC-Co | | | HFD | | | HFD-Co | | |
|---|---|---|---|---|---|---|---|---|---|---|---|---|
| | 1 m | 2 m | 3 m | 1 m | 2 m | 3 m | 1 m | 2 m | 3 m | 1 m | 2 m | 3 m |
| Insul. | 465 ± 17 | 440 ± 11 | 483 ± 32 | 472 ± 18 | 462 ± 33 | 518 ± 18 | 636 ± 36§ | 736 ± 57§ | 784 ± 109§ | 671 ± 41# | 732 ± 62# | 836 ± 105#* |
| Lept. | 741 ± 505 | 683 ± 376 | 760 ± 385 | 940 ± 263§ | 626 ± 503 | 384 ± 153 | 1626 ± 589§ | 2023 ± 451§ | 2347 ± 254§ | 2209 ± 636#* | 1177 ± 418#* | 3474 ± 421#* |
| IgG | 1411 ± 82 | 1199 ± 73 | 2836 ± 857 | 1468 ± 91 | 1360 ± 388 | 2231 ± 561 | 1690 ± 522 | 3199 ± 1230§ | 5933 ± 947§ | 991 ± 98#* | 2211 ± 384#* | 2362 ± 514#* |
| IFN-γ | 36 ± 25 | 230 ± 106 | 255 ± 420 | 13 ± 8§ | 7 ± 5§ | 14 ± 7§ | 55 ± 45 | 176 ± 80 | 70 ± 30 | 4 ± 2* | 7 ± 3* | 23 ± 30* |
| IL-6 | 4 ± 1 | 8 ± 2 | 9 ± 4 | 19 ± 8§ | 21 ± 10§ | 8 ± 5 | 2 ± 1 | 4 ± 1 | 2 ± 1 | 16 ± 6* | 18 ± 5* | 22 ± 4* |
| IP10 | 73 ± 17 | 108 ± 17 | 138 ± 25 | 100 ± 33 | 87 ± 13 | 95 ± 10 | 81 ± 18 | 93 ± 12 | 100 ± 19 | 96 ± 15 | 110 ± 18 | 126 ± 7 |
| RANTES | 22 ± 7 | 26 ± 10 | 22 ± 8 | 16 ± 1 | 13 ± 4 | 9 ± 2 | 14 ± 5 | 21 ± 4 | 15 ± 3 | 17 ± 4 | 21 ± 4 | 15 ± 3 |
| MIG | 22 ± 6 | 28 ± 5 | 46 ± 22 | 24 ± 4 | 23 ± 5 | 33 ± 12 | 25 ± 11 | 32 ± 9 | 30 ± 8 | 20 ± 3 | 30 ± 9 | 27 ± 8 |
| α-PG | 1.45± 0.24 | 1.54± 0.24 | 1.49± 0.14 | 3.89± 2.44§ | 3.76± 2.63§ | 3.58± 1.82§ | 1.19± 0.11 | 1.12± 0.25 | 1.92± 1.70 | 1.79± 0.45# | 1.17± 0.27# | 1.31± 0.29# |

N = 6 per group;
Data as mean ± SEM
*$P < 0.05$ when compared to HFD,
§$P < 0.05$ when compared to NC and
$P < 0.05$ when compared to NC-Co
Param.: parameters
1 m: 1 month
2 m: 2 months
3 m: 3 months
Insul.: Insulinemia (pg/ml)
Lept.: Leptinemia (pg/ml)
IgG (μg/ml)
IFN-γ (pg/ml)
IL-6 (pg/ml)
IP10 (pg/ml)
RANTES (pg/ml)
MIG (pg/ml)
α-PG: antibodies anti-PG (EI)

To demonstrate that periodontal pathogen-induced periodontitis may represent an aggravating risk factor for diet-induced metabolic diseases, the inventors characterized glucose metabolism in response to the nutritional stress. The data obtained show that periodontitis aggravated the HFD- Immunotherapy.

Cervical lymph nodes were harvested both from mice colonized with bacteria mixture as described in Example 1, or not colonized. Cervical lymph node cells ($10^7$ total) were injected into the peritoneal cavity from mice with periodontitis (PTC) or without (HTC) and intraperitoneal glucose-tolerance test (IPGTT) was assessed after transfer and after colonization by periodontal pathogens.

Intraperitoneal Glucose-Tolerance Test (IPGTT) and In Vivo Glucose Infusion Rate.

See example 1.

Statistical Analysis.

See example 1.

Results

To demonstrate that the adaptive immune system was triggered by the change in periodontal microbial ecology and was a causal mechanism responsible for the deleterious impact of the periodontal pathogens on metabolic disease, the inventors first transferred the cervical lymph-node cells from mice with or without periodontitis to healthy recipient mice (FIG. 9A). In such conditions the glucose-tolerance was similar in both groups of recipient mice, suggesting that another confounding factor was required to trigger the metabolic disease. Hence, the inventors challenged the recipient mice with the periodontal pathogens 6 weeks after the cell transfer (FIG. 9A) and demonstrated that the glucose-tolerance was improved in mice which received the immune cells from the infected mouse when compared to those which received immune cells from a non-infected mouse (FIG. 9B,C). Body weight gain was not significantly affected. The transfer of immune cells by itself, without colonizing the recipient mice, is not sufficient to impact on glucose tolerance (FIG. 9B,C). However glucose metabolism could be impacted when the immune cells were specifically adapted to the periodontal pathogens. This suggests that both nutritional stress and periodontitis are required factors to trigger metabolic phenotypes.

Example 3: A Treatment with Inactivated *Porphyromonas gingivalis* Prior to the Periodontal Infection Induces Specific Antibodies Against *Porphyromonas gingivalis* and Protects the Mouse from Periodontitis-Induced Dysmetabolism Materials and Methods Animals and Experimental Procedures.

See example 1.

Immunization.

An injection of $10^6$ CFU of *Porphyromonas gingivalis, Fusobacterium nucleatum* or *Prevotella intermedia* or the mix of the three bacteria, inactivated by oxygen-exposition during 48 hours, was given in the footpad muscle. Control mice were injected with saline. Then, periodontitis was induced (as described in Example 1) one month after the immunization in 3 months HFD-fed mice.

Intraperitoneal Glucose-Tolerance Test (IPGTT) and In Vivo Glucose Infusion Rate.

See example 1.

Anti-*Porphyromonas gingivalis* Antibodies Measurement.

Immunoglobulin G antibodies specific to LPS of *P. gingivalis* were measured using a homemade ELISA. The wells of 96-well flat-bottom microtiter plates were coated in triplicates with LPS of *P. gingivalis*. After washing and blocking the plates, serum samples were added to individual wells and specific mouse IgG antibodies were detected with an alkaline phosphatase-conjugated anti-mouse immunoglobulin. The absorbance was read at 405 nm using an ELISA plate reader. The results were expressed as an ELISA index (EI), which was the mean OD 405 of a given serum sample divided by the mean OD 405 of the calibrator (reference serum) (Hitchon et al. (2010) *J. Rheumatology* 37:1105-1112).

Statistical Analysis.

See example 1.

Results

In a second set of experiments, to further validate the role of the adaptive immune system on the control of glucose-tolerance, the inventors immunized the lymphocytes to the periodontal pathogens by treating mice with different sets of inactivated periodontal pathogens (FIG. 10A). The intramuscular treatment with the three inactivated periodontal pathogens prevented the above reported aggravating effects of periodontitis on HFD-induced glucose-intolerance at 1 month (FIGS. 11A-F), 2 months and 3 months (FIGS. 10B-F). Importantly, this preventive effect was due to *Porphyromonas gingivalis* since the treatment of the mice with this unique bacteria was sufficient to protect against periodontitis-induced metabolic diseases. Moreover, the specific treatment by *Porphyromonas gingivalis* prevented the decreased of antibodies anti-Pg observed on HFD after periodontal colonization at 1 and 3 months (FIGS. 11G and 10G). At 3 months of HFD, the treatment by PG protected against the periodontal colonization-induced alveolar bone loss in periodontal tissue (FIG. 10H).

The invention claimed is:

1. A method for preventing aggravating effects of periodontitis on high fat diet-induced glucose intolerance in a subject in need thereof having periodontitis and being under high fat diet, said method comprising administering a prophylactically or therapeutically effective amount of a vaccine composition comprising attenuated *Porphyromonas gingivalis* or inactivated *Porphyromonas gingivalis* in said subject.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic forward primer TNF-alpha

<400> SEQUENCE: 1
tgggacagtg acctggactg t                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetic reverse primer TNF-alpha

```
<400> SEQUENCE: 2
tcggaaagcc catttgagt                                          19

<210> SEQ ID NO 3
<211> LENGTH: 20
<212> TYPE: DNA
<213> ORGANISM: Artificial Sequence
<220> FEATURE:
<223> OTHER INFORMATION: Synthetic forward primer IL-1beta

<400> SEQUENCE: 3
tcgctcaggg tcacaagaaa                                         20

<210> SEQ ID NO 4
<211> LENGTH: 22
<212> TYPE: DNA
<213> ORGANISM: Artificial Sequence
<220> FEATURE:
<223> OTHER INFORMATION: Synthetic reverse primer IL-1beta

<400> SEQUENCE: 4
catcagaggc aaggaggaaa ac                                      22

<210> SEQ ID NO 5
<211> LENGTH: 21
<212> TYPE: DNA
<213> ORGANISM: Artificial Sequence
<220> FEATURE:
<223> OTHER INFORMATION: Synthetic forward primer PAI-1

<400> SEQUENCE: 5
acagcctttg tcatctcagc c                                       21

<210> SEQ ID NO 6
<211> LENGTH: 21
<212> TYPE: DNA
<213> ORGANISM: Artificial Sequence
<220> FEATURE:
<223> OTHER INFORMATION: Synthetic reverse primer PAI-1

<400> SEQUENCE: 6
ccgaaccaca aagagaaagg a                                       21

<210> SEQ ID NO 7
<211> LENGTH: 25
<212> TYPE: DNA
<213> ORGANISM: Artificial Sequence
<220> FEATURE:
<223> OTHER INFORMATION: Synthetic forward primer IL-6

<400> SEQUENCE: 7
acaagtcgga ggcttaatta cacat                                   25

<210> SEQ ID NO 8
<211> LENGTH: 22
<212> TYPE: DNA
<213> ORGANISM: Artificial Sequence
<220> FEATURE:
<223> OTHER INFORMATION: Synthetic reverse primer IL-6

<400> SEQUENCE: 8
ttgccattgc acaactcttt tc                                      22

<210> SEQ ID NO 9
<211> LENGTH: 23
```

```
<212> TYPE: DNA
<213> ORGANISM: Artificial Sequence
<220> FEATURE:
<223> OTHER INFORMATION: Synthetic forward primer RPL19

<400> SEQUENCE: 9
gaaggtcaaa gggaatgtgt tca                                         23

<210> SEQ ID NO 10
<211> LENGTH: 21
<212> TYPE: DNA
<213> ORGANISM: Artificial Sequence
<220> FEATURE:
<223> OTHER INFORMATION: Synthetic reverse primer RPL19

<400> SEQUENCE: 10
ccttgtctgc cttcagcttg t                                           21
```